(12) United States Patent
Kim et al.

(10) Patent No.: US 11,932,839 B2
(45) Date of Patent: Mar. 19, 2024

(54) MICROENGINEERED TISSUE BARRIER SYSTEM

(71) Applicant: Georgia Tech Research Corporation, Atlanta, GA (US)

(72) Inventors: YongTae Kim, Atlanta, GA (US); Song Ih Ahn, Atlanta, GA (US); Taeyoung Kim, Atlanta, GA (US); Jeongkee Yoon, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 297 days.

(21) Appl. No.: 17/114,282

(22) Filed: Dec. 7, 2020

(65) Prior Publication Data
US 2021/0171889 A1 Jun. 10, 2021

Related U.S. Application Data

(60) Provisional application No. 62/945,501, filed on Dec. 9, 2019.

(51) Int. Cl.
| | | |
|---|---|---|
| C12M 1/12 | (2006.01) | |
| C12M 3/00 | (2006.01) | |
| C12M 3/06 | (2006.01) | |
| G01N 33/50 | (2006.01) | |

(52) U.S. Cl.
CPC ............ C12M 23/16 (2013.01); C12M 23/42 (2013.01); C12M 25/02 (2013.01); G01N 33/502 (2013.01)

(58) Field of Classification Search
CPC ...... C12M 23/16; C12M 23/42; C12M 25/02; C12M 23/34; C12M 35/08; C12M 21/08; C12M 23/44; C12M 33/14; C12M 41/44; G01N 33/502; G01N 33/5082; C12N 5/0062

USPC ............................................ 435/283.1, 289.1
See application file for complete search history.

(56) References Cited

U.S. PATENT DOCUMENTS

| | | | |
|---|---|---|---|
| 5,863,792 A * | 1/1999 | Tyndorf | C12M 23/12 435/297.5 |
| 9,518,977 B2 * | 12/2016 | Folch | B01L 3/502715 |
| 2019/0032021 A1 | 1/2019 | Ingber et al. | |
| 2019/0093077 A1 * | 3/2019 | Hamilton | A61K 35/407 |
| 2019/0177678 A1 * | 6/2019 | Bigliardi | C12M 23/16 |

FOREIGN PATENT DOCUMENTS

WO    WO-2015/138034 A2    9/2015

OTHER PUBLICATIONS

Lee et al., Biomed Microdevices 19:100, pp. 1-13. (Year: 2017).*
International Search Report and Written Opinion for International Application No. PCT/US2020/063636 dated Apr. 5, 2021.

* cited by examiner

*Primary Examiner* — Liban M Hassan
(74) *Attorney, Agent, or Firm* — Fenwick & West LLP

(57) ABSTRACT

The present invention relates to a microfluidic device for simulating the structure and function of an in vivo tissue barrier. Specifically, the present invention relates to a microfluidic device that can be used as a model for new drug development and toxicity assessment and the like by simulating the structure and function of a two-dimensional-three-dimensional connective tissue barrier or a three-dimensional tissue barrier and thus replacing animal models, a method of culturing cells in the microfluidic device, and a method of simulating an organ or a body part using the microfluidic device.

16 Claims, 41 Drawing Sheets

MICROENGINEERED TISSUE BARRIER SYSTEM

CROSS-REFERENCE TO RELATED APPLICATION

This application claims the benefit of the following U.S. Provisional Application No. 62/945,501, filed Dec. 9, 2019, the entire contents of which are incorporated herein by reference.

GOVERNMENT LICENSE RIGHTS

This invention was made with government support under (1DP2HL142050-01) awarded by Department of Health and Human Services. The government has certain rights in the invention.

BACKGROUND

Organ-on-a-chip was developed in which an organ tissue is integrated in a chip form in order to solve ethical problems and problems due to differences between different species in the use of experimental animal models for examining efficacy and side effects of a drug. Organ-on-a-chip is a technology that implements a desired function by culturing cells constituting a specific organ in a small chip, and thus simulating the morphology and physiological property of that organ. Organ-on-a-chip can be used to study in detail the cell behavior of a specific organ and the mechanism of physicochemical reactions in microenvironment, and can be used as a model for new drug development and toxicity assessment.

In the development of organ-on-a-chip, a cell culture model using a conventional two-dimensional (2D) cell culture has a problem in not being able to explain tissue-specific differentiated functions of many cell types or not being able to accurately predict tissue function and drug activity in vivo since it uses a petri dish to culture cells on the bottom of the dish in two dimensions.

In particular, in the case of brain tissue cells having neurons, astrocytes and the like having three-dimensional contact in vivo, due to the limitation of the above two-dimensional cell culture model, there is an increasing need for a three-dimensional cell culture model that well simulates the spatial structure and biochemical complexity of a living tissue.

Since the three-dimensional cell culture model well mimics the in vivo situation, it can implement the complexity of directional growth and intercellular connectivity in in vitro experiments, and it is useful for capturing the signaling pathway and drug responsiveness of various disease states well compared to the two-dimensional cell culture model in studying tissue functions on a molecular basis.

On the other hand, the microfluidic engineering technology developed along with the semiconductor process technology enabled mass production of a structure having a micro-level size with high accuracy. In particular, photolithography and soft lithography technologies have made it possible to easily produce microchannel structures through stamping using semi-permanent molds, and through this, there have been attempts to simulate microstructures such as blood vessels of the human body and cell layers of organs in vitro.

Existing research has been carried out in the form of preparing a chip having a polydimethylsiloxane (PDMS) microchannel and a porous membrane using photolithography or soft lithography technology, and implementing the cell layer structure of an organ through cell culture inside the chip. However, in an organ-on-a-chip using a microfluidic device made of PDMS material, there are many cases in which drugs or proteins were adsorbed on the surface of PDMS and disappeared, constituting a limitation that is difficult to overcome when attempting to simulate an in vivo environment that will have greater applicability in the actual pharmaceutical industry.

Thus, a need exists for an organ-on-a-chip that more closely simulates the structure and function of an in vivo two-dimensional-three-dimensional connective tissue barrier or a three-dimensional tissue barrier.

SUMMARY

The present disclosure relates to a microfluidic device for simulating the structure and function of an in vivo tissue barrier. Specifically, the present disclosure relates to a microfluidic device that can be used as a model for new drug development and toxicity assessment and the like by simulating the structure and function of a two-dimensional-three-dimensional connective tissue barrier or a three-dimensional tissue barrier and thus replacing animal models, a method of culturing cells in the microfluidic device, and a method of simulating an organ or a body part using the microfluidic device. Therefore, the present disclosure provides an improvement to the organ-on-a-chip that uses a conventional microfluidic device. The microfluidic device described herein more closely simulates the structure and function of an in vivo two-dimensional-three-dimensional connective tissue barrier or a three-dimensional tissue barrier.

An object of the present disclosure is to provide a microfluidic device that exhibits more similar structure and function to the in vivo tissue barrier compared to the conventional organ-on-a-chip by solving ethical problems and problems due to differences between different species in the use of experimental animal models and forming the structure of a two-dimensional-three-dimensional connective tissue barrier or a three-dimensional tissue barrier.

The present disclosure provides a microfluidic device comprising an insert comprising a first central channel; a base comprising a second central channel, a third side channel, a fourth side channel, a fifth passage channel connecting the second central channel and the third side channel, and a sixth passage channel connecting the second central channel and the fourth side channel; and a porous membrane positioned between the insert and the base.

The present disclosure provides a method of culturing cells in a microfluidic device, the method comprising a step of assembling the microfluidic device; a step of injecting second cells into the second central channel and then inverting the microfluidic device and culturing them; a step of injecting hydrogel comprising third cells into the second central channel and then culturing them; and a step of inverting the microfluidic device and then injecting first cells into the first central channel and culturing them.

In addition, the present disclosure provides a method of simulating the structure and function of an organ or a body part using the microfluidic device, wherein the method of simulating an organ or a body part comprises a step of perfusing a first fluid through the first central channel; and a step of perfusing a second fluid into a third side channel, a second central channel, and a fourth side channel.

The microfluidic device of the present disclosure can be used for the evaluation of drug efficacy by simulating the main structures of various in vivo tissue barriers including the blood-brain barrier and material transport phenomenon.

The microfluidic device of the present disclosure enables precise quantification of the distribution of nanoparticles around the tissue barrier, and since the insert is detachable from the base, cells contained in the microfluidic device can be selectively separated without damage and used for analysis. In addition, the insert is capable of being separated from the base, subjected to a necessary treatment such as drug application, and then reassembled to observe a cellular reaction.

The microfluidic device of the present disclosure is capable of three-dimensional culture of cells, thereby implementing the spatial structure and biochemical complexity of cells in vivo and thus better simulating the structure and function of the tissue barrier.

BRIEF DESCRIPTION OF DRAWINGS

Throughout the figures, the following labels are used to identify specific features.
- 100: insert
- 101: first fastening head
- 110: first central channel
- 111: first cell
- 112: inlet of the first central channel
- 113: outlet of the first central channel
- 200: base
- 201: insert insertion groove
- 202: second fastening head
- 210: second central channel
- 211: second cell
- 212: third cell
- 213: hydrogel
- 214: inlet of the second central channel
- 215: outlet of the second central channel
- 220: third side channel
- 221: inlet of the third side channel
- 222: outlet of the third side channel
- 230: fourth side channel
- 231: inlet of the fourth side channel
- 232: outlet of the fourth side channel
- 240: fifth passage channel
- 250: sixth passage channel
- 260: seventh passage channel
- 270: eighth passage channel
- 280: first fluid reservoir
- 290: second fluid reservoir
- 300: porous membrane
- 400: bottom part
- 500: cover
- 501: inlet of the first central channel in the cover
- 502: outlet of the first central channel in the cover

DETAILED DESCRIPTION

Figure 1:
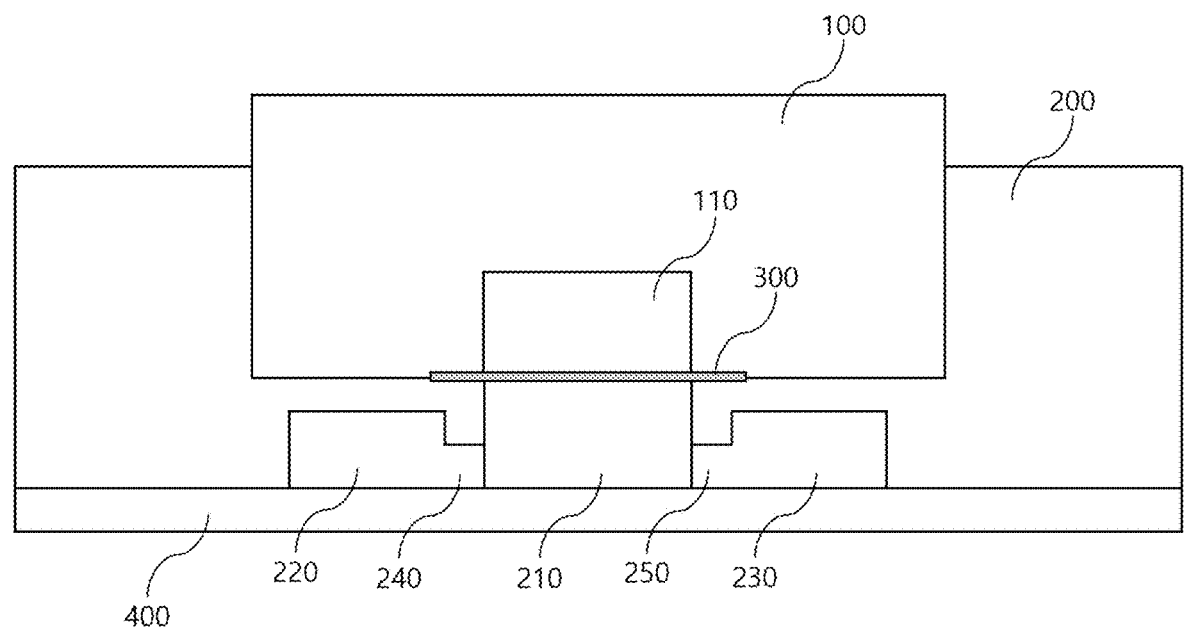
FIG. 1 is a cross-sectional view of a microfluidic device.

Hereinafter, the embodiments and examples of the present application will be described in detail with reference to the accompanying drawings so that those of ordinary skill in the art to which the present disclosure belongs can easily practice the present disclosure. However, the present application can be implemented in various forms and is not limited to the embodiments and examples described herein.

Throughout the specification of the present application, unless otherwise stated, when a certain part "comprises" a certain constituent element, it means that the certain part may further comprise other constituent elements rather than exclude other constituent elements.

The present disclosure provides a microfluidic device comprising an insert comprising a first central channel; a base comprising a second central channel, a third side channel, a fourth side channel, a fifth passage channel connecting the second central channel and the third side channel, and a sixth passage channel connecting the second central channel and the fourth side channel; and a porous membrane positioned between the insert and the base.

As used herein, the term "microfluidic device" refers to a device comprising microchannels and the like provided to allow fluid to flow on a substrate made of various materials including plastic, glass, metal, or silicon including organic polymer materials.

As used herein, the term "microchannel" refers to a channel of microscopic size having a dimension of millimeters, micrometers, or nanometers through which fluid can flow.

As used herein, the term "insert" may refer to an object in a shape that is capable of being inserted into a groove formed in another object, but is not limited thereto.

In some embodiments, the insert is detachable from the base, and the base may comprise a groove into which the insert is capable of being inserted. Preferably, the insert comprises a first fastening head, the base comprises a second fastening head, wherein the first fastening head and the second fastening head are hooked to each other so that the insert and the base can be attached and detached by a snap fit. In this case, in order to prevent leakage between the first central channel and the second central channel, the porous membrane may serve as a gasket by receiving a strong pressure between the insert and the base.

As used herein, the "fastening head" may be made of a material having elasticity such as plastic, rubber, silicon and the like, and each may be elastically deformed to achieve the attachment and detachment by a snap fit, but is not limited thereto.

As used herein, the term "snap fit" refers to a fastening manner in which a fastening force is formed by the interaction of components or structures that are capable of securing or fastening to each other (e.g., grooves that are hooked to each other without additional parts or fastening instruments).

In some embodiments, the third side channel and the fourth side channel do not contact the porous membrane. Preferably, the third side channel and the fourth side channel may have a lower height than that of the second central channel, and more preferably, the ratio of the height of the second central channel to the height of the third side channel and the fourth side channel may be between 1:0.1 and 1:0.9.

In some embodiments, the first central channel, the second central channel, the third side channel, and the fourth side channel comprise an inlet and an outlet capable of inducing and controlling the perfusion of the liquid agent. The method capable of inducing and controlling the perfusion may include a method of using a hydrostatic pressure difference between the inlet and the outlet, and a method of connecting an external pump to the inlet and the outlet, but is not limited thereto.

In some embodiments, the fifth passage channel and the sixth passage channel have a lower channel height than those of the second central channel, the third side channel, and the fourth side channel. Preferably, the ratio of the height of the second central channel and the height of the fifth passage channel and the sixth passage channel may be between 1:0.03 and 1:0.2, and the ratio of the height of the third side channel and the fourth side channel and the height of the fifth passage channel and the sixth passage channel may be between 1:0.03 and 1:0.7.

In some embodiments, the base comprises a first fluid reservoir and a second fluid reservoir. In addition, the base may comprise a seventh passage channel connecting the third side channel and the first fluid reservoir, and an eighth passage channel connecting the fourth side channel and the second fluid reservoir. Preferably, the seventh passage channel and the eighth passage channel may have a lower channel height than those of the second central channel, the third side channel, and the fourth side channel. Preferably, the ratio of the height of the second central channel and the height of the seventh passage channel and the eighth passage channel may be between 1:0.02 and 1:0.05, and the ratio of the height of the third side channel and the fourth side channel and the height of the seventh passage channel and the eighth passage channel may be between 1:0.02 and 1:0.5. More preferably, the height of the seventh passage channel and the eighth passage channel may be 50 μm or less.

In some embodiments, the seventh passage channel and the eighth passage channel are perpendicular to the direction of the second central channel.

In some embodiments, the microfluidic device is made of plastic, glass, metal, or silicon, but is not limited thereto. Preferably, it may be made of plastic using injection molding technology.

In some embodiments, the first central channel comprises tissue barrier cells. The tissue barrier cells may include vascular endothelial cells; skin cells; cancer cells; secretory gland cells; muscle cells; and epithelial cells of bronchi, large intestine, small intestine, pancreas, and kidney. Preferably, it may be a vascular endothelial cell. More preferably, it may be a human brain microvascular endothelial cell (HBMEC).

As used herein, the term "cell" refers to a biological cell, including a plant cell, an animal cell (such as, a mammalian cell), a bacterial cell and a fungal cell and the like.

As used herein, the term "tissue barrier cell" refers to a cell that plays a role in maintaining a specific structure of a tissue, and plays a role in protecting the tissue from external stimuli. In addition, it refers to a cell that plays a role in selectively permeating a substance using a strong binding force between tissue barrier cells or an extracellular matrix, and maintaining homeostasis in the concentration of the substance in the tissue. The tissue barrier cells include epithelial tissue cells and vascular endothelial cells.

In some embodiments, the second central channel comprises internal tissue cells and hydrogel.

The internal tissue cells may include astrocytes, pericytes, nerve cells, neural stem cells, glial cells, cardiac myocytes, smooth muscle cells, intestinal epithelial cells, keratinocytes, skin fibroblasts, podocytes, and glomerular endothelial cells. Preferably, it may be an astrocyte and a pericyte. More preferably, it may be a human astrocyte (HA) and a human brain vascular pericyte (HBVP).

As used herein, the term "internal tissue cell" refers to a cell that makes up the organs and tissues of the human body, and includes all cells that make up the human body tissue including, but not limited to, epithelial tissue, muscle tissue, nervous tissue, or connective tissue.

The hydrogel may be one or more selected from collagen, laminin, hyaluronic acid, mineral, fibrin, fibronectin, elastin, peptide, polyethylene glycol, and alginate. Preferably, the hydrogel may be collagen gel, fibrin gel, laminin gel, Matrigel, animal derived tumor basement membrane extract gel, tissue decellularized extracellular matrix gel, peptide gel, polyethylene glycol gel, or alginate gel, but is not limited thereto. More preferably, it is laminin gel or Matrigel.

The hydrogel may be spatially confined in the second central channel by surface tension due to a height difference between the second central channel and the fifth passage channel and a height difference between the second central channel and the sixth passage channel.

As used herein, the term "hydrogel" is a hydrophilic polymer crosslinked by cohesive force such as covalent bonds, hydrogen bonds, van der waals bonds, or physical bonds, and refers to a material having a three-dimensional polymer network structure that is capable of swelling since it contains a large amount of water in an aqueous solution therein.

In some embodiments, each of one or more cells selected from cells included in the first central channel, cells included in the second central channel, and cells attached to the porous membrane are separated by separating the insert from the base, and cell analysis such as gene analysis may be performed using the separated cells.

In some embodiments, the insert is capable of being separated from the base, and being subjected to a necessary treatment such as drug application to the first central channel, and then being reassembled to the base to observe a cellular reaction.

The present disclosure provides a method of culturing cells in a microfluidic device, the method comprising a step of assembling a microfluidic device, wherein the microfluidic device is comprises an insert comprising a first central channel; a base comprising a second central channel, a third side channel, and a fourth side channel; and a porous membrane positioned between the insert and the base, wherein the insert is detachable from the base; a step of injecting second cells into the second central channel and then inverting the microfluidic device and culturing them; a step of injecting hydrogel comprising third cells into the second central channel and then culturing them; and a step of inverting the microfluidic device and then injecting first cells into the first central channel and culturing them.

In some embodiments, the first central channel, the second central channel, the third side channel, and the fourth side channel include an inlet and an outlet capable of inducing and controlling the perfusion of the liquid agent, and the second cells and the hydrogel comprising the third cells may be injected through the inlet of the second central channel, and the first cells may be injected through the inlet of the first central channel.

In some embodiments, the first cells are selected from vascular endothelial cells; skin cells; cancer cells; secretory gland cells; muscle cells; and epithelial cells of bronchi, large intestine, small intestine, pancreas, or kidney; the second cells may be selected from pericytes, glial cells, cardiac myocytes, smooth muscle cells, intestinal epithelial cells, keratinocytes, skin fibroblasts, podocytes, and glomerular endothelial cells; and the third cells may be selected from astrocytes, nerve cells, and neural stem cells. Preferably, the first cells may be vascular endothelial cells, the second cells may be pericytes, and the third cells may be astrocytes. More preferably, the first cells may be human brain microvascular endothelial cells (HBMEC), the second cells may be human brain vascular pericytes (HBVP), and the third cells may be human astrocytes (HA).

The present disclosure provides a method of culturing cells in a microfluidic device, the method comprising a step of assembling a microfluidic device, wherein the microfluidic device is comprises comprising an insert comprising a first central channel; a base comprising a second central channel, a third side channel, and a fourth side channel; and a porous membrane positioned between the insert and the base, wherein the insert is detachable from the base; a step of injecting 1 to 50 µl of human brain vascular pericytes (HBVP) at a concentration of $10^4$ cells/ml or more into the second central channel and then inverting the microfluidic device and culturing them; a step of injecting hydrogel comprising 1 to 50 µl of human astrocytes (HA) at a concentration of $10^3$ cells/ml or more into the second central channel and then culturing them; and a step of inverting the microfluidic device and then injecting 1 to 50 µl of human brain microvascular endothelial cells (HBMEC) at a concentration of $10^5$ cells/ml or more into the first central channel and culturing them.

The present disclosure provides a method of simulating an organ or a body part in a microfluidic device, wherein the microfluidic device is comprises an insert comprising a first central channel; a base comprising a second central channel, a third side channel, a fourth side channel, a first fluid reservoir, and a second fluid reservoir; and a porous membrane positioned between the insert and the base, wherein the insert is detachable from the base, wherein the method comprises a step of perfusing a first fluid through the first central channel; and a step of injecting a second fluid into the first fluid reservoir to sequentially reach the third side channel, the second central channel, the fourth side channel, and the second fluid reservoir. The organ or body part may include blood-brain barrier, lung, liver, heart, retina, large intestine, small intestine, pancreas, and kidney, but is not limited thereto. Preferably, the organ or body part is blood-brain barrier (BBB).

In some embodiments, the base comprises a fifth passage channel connecting the second central channel and the third side channel, a sixth passage channel connecting the second central channel and the fourth side channel, a seventh passage channel connecting the third side channel and the first fluid reservoir, and an eighth passage channel connecting the fourth side channel and the second fluid reservoir.

In some embodiments, the first fluid is perfused with a shear stress of 1 to 10 dyne/$cm^2$, and preferably, it may be perfused with a shear stress of 4 to 6 dyne/$cm^2$. The flow of the first fluid may play a role in simulating the flow of blood in vivo.

In some embodiments, the flow rate of the second fluid is maintained at 1 to 100 µl/h for at least 12 hours by using the hydrostatic pressure difference between the first fluid reservoir and the second fluid reservoir, and preferably, it may be maintained at 10 to 15 µl/h. The flow of the second fluid may play a role in simulating the interstitial flow in vivo.

The present disclosure provides a method of analyzing physiological, pharmacological or toxicological effects of an agent, said method comprising: a) providing a microfluidic device according to Claim 1; b) introducing the agent into the microfluidic device; and c) evaluating physiological, pharmacological or toxicological effects of the agent. The above agent may include a drug, toxin or pathogen.

Hereinafter, the microfluidic device of the present disclosure will be described in detail with reference to the drawings. The present disclosure may include a microfluidic device embodied in the form of FIGS. 1 to 25, but is not limited thereto. In particular, although specific examples of the microfluidic device of the present disclosure are illustrated in FIGS. 12 to 25, the present disclosure is not limited to the specific examples, and includes various modifications capable of being made by those of ordinary skill in the art to which the present disclosure belongs.

The microfluidic device according to one example of the present disclosure comprises an insert (100), a base (200), and a porous membrane (300) positioned between the insert (100) and the base (200).

Referring to FIG. 1, the insert (100) comprises a first central channel (110), and the base (200) comprises a second central channel (210), a third side channel (220), a fourth side channel (230), a fifth passage channel (240) connecting the second central channel (210) and the third side channel (220), and a sixth passage channel (250) connecting the second central channel (210) and the fourth side channel (230). In some embodiments, a bottom part (400) is attached to the lower end of the base (200).

Figure 2:
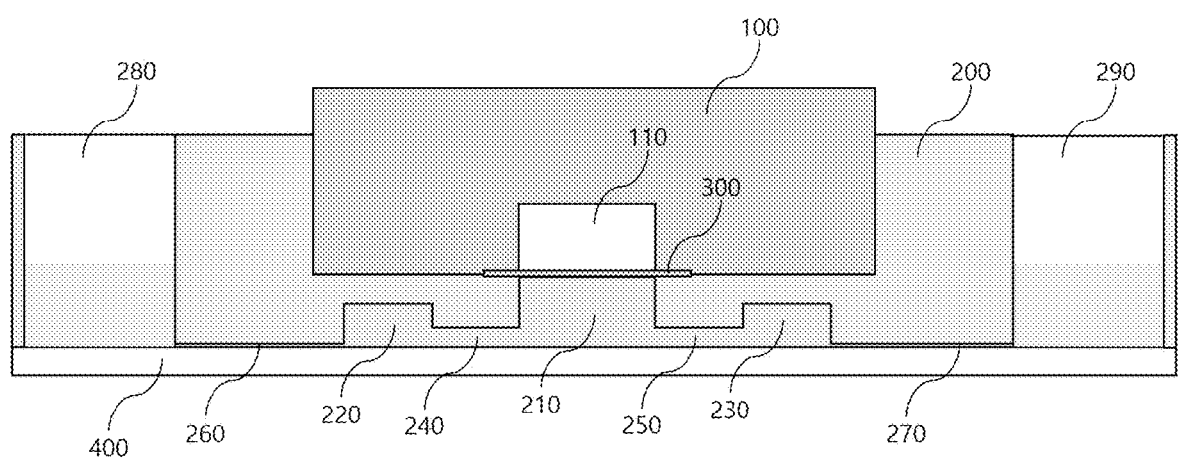
FIG. 2 is a cross-sectional view of a microfluidic device.
Figure 3:
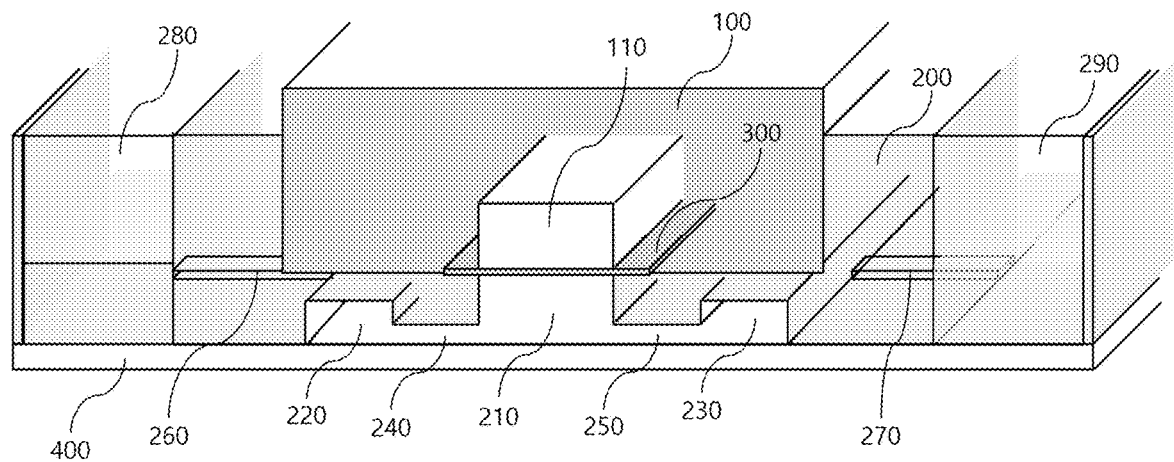
FIG. 3 is a perspective view of a microfluidic device.

Referring to FIGS. 2 and 3, the base (200) of the microfluidic device may comprise a first fluid reservoir (280) and a second fluid reservoir (290), and it may comprise a seventh passage channel (260) connecting the third side channel (220) and the first fluid reservoir (280), and an eighth passage channel (270) connecting the fourth side channel (230) and the second fluid reservoir (290).

Figure 4:
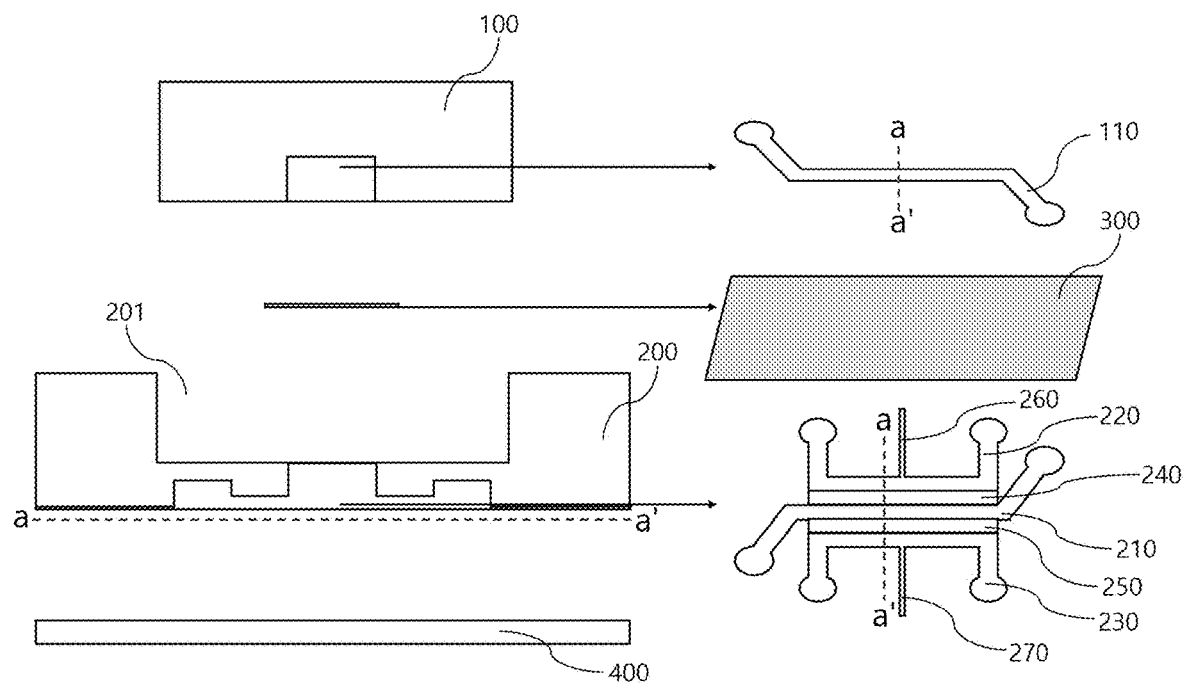
FIG. 4 is an exploded view of a microfluidic device.
Figure 5:
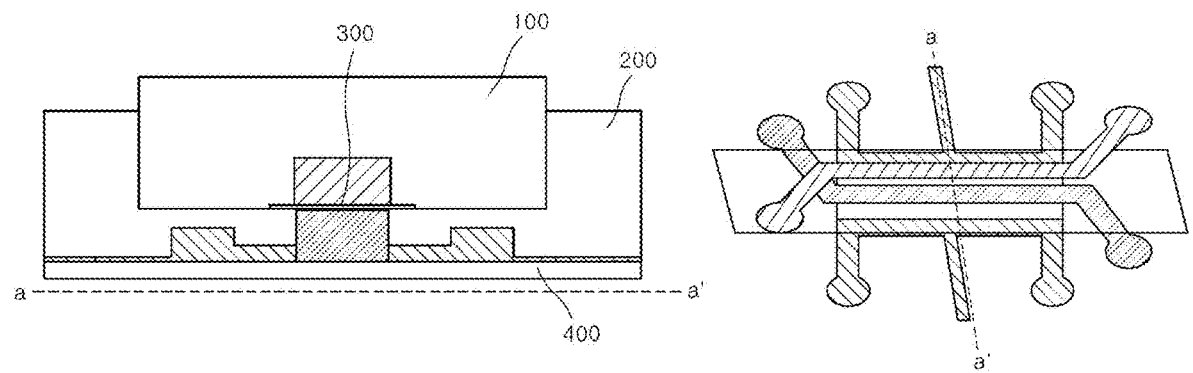
FIG. 5 is a combined view of a microfluidic device.

Referring to FIGS. 4 and 5, the porous membrane (300) of the microfluidic device exists between the first central channel (110) and the second central channel (210), and the seventh passage channel (260) and the eighth passage channel (270) may be formed perpendicular to the direction of the second central channel (210).

Figure 6:
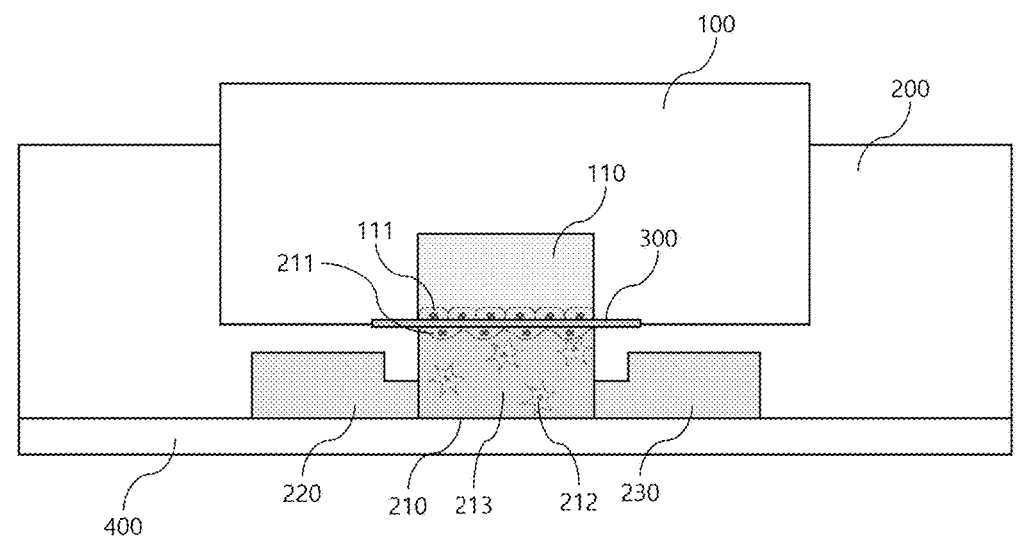
FIG. 6 is a cross-sectional view of a microfluidic device comprising cells and hydrogel
Figure 7:
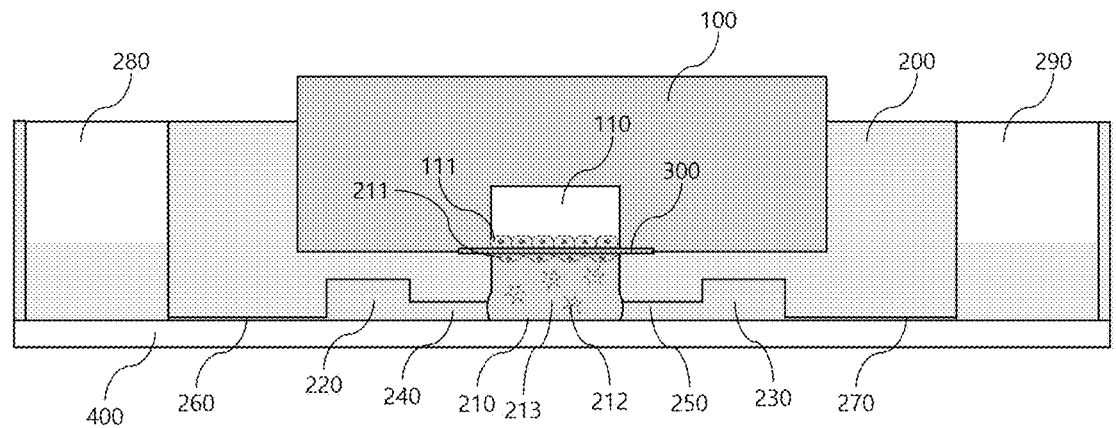
FIG. 7 is a cross-sectional view of a microfluidic device comprising cells and hydrogel.
Figure 8:
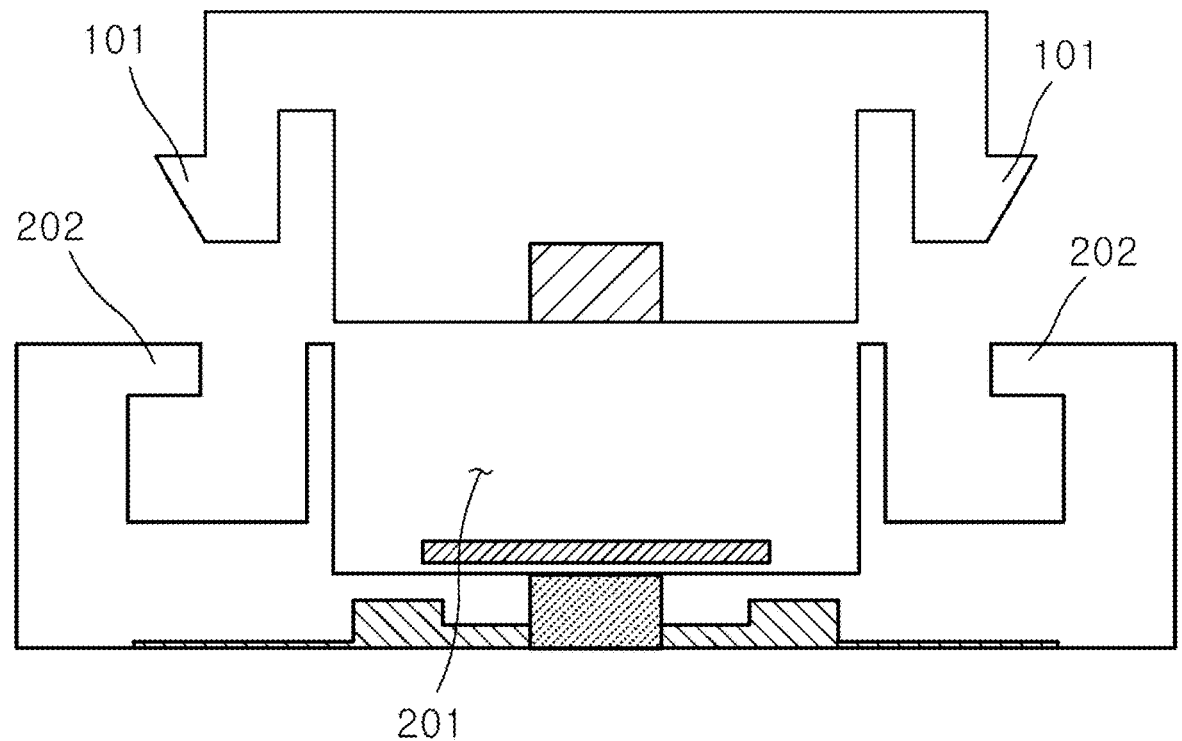
FIG. 8 is a cross-section view showing a configuration for attaching and detaching an insert and a base.
Figure 9:
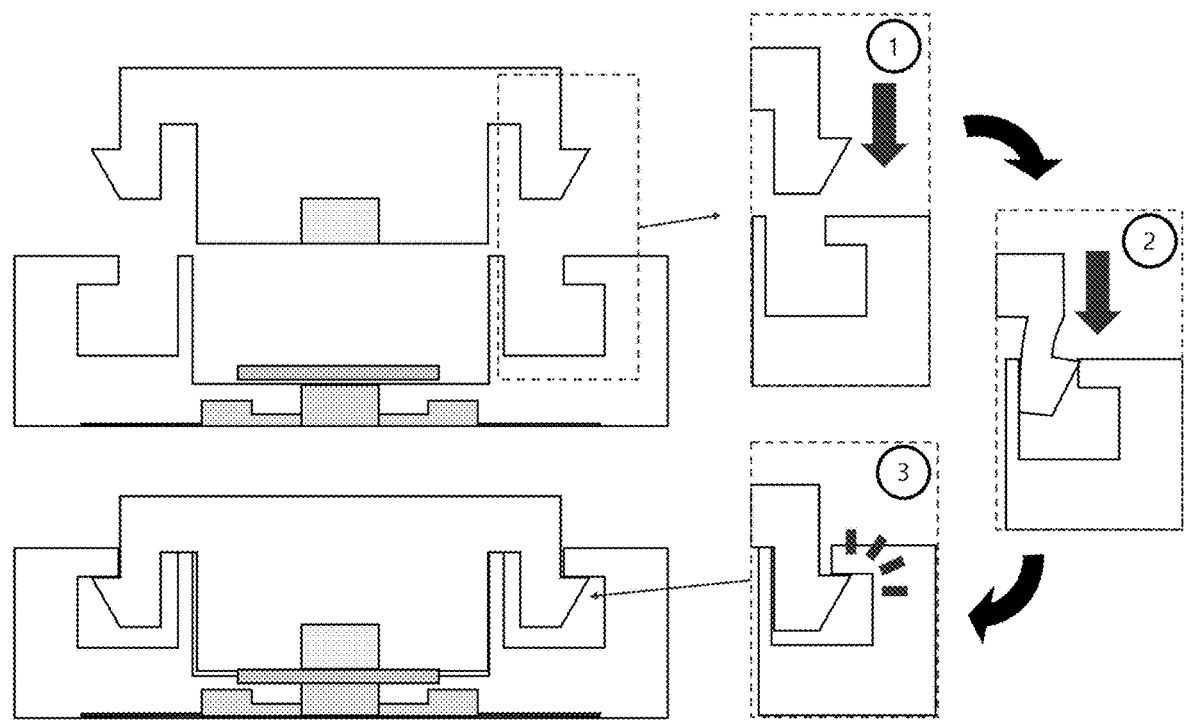
FIG. 9 is a cross-sectional view showing a configuration for attaching and detaching an insert and a base and an attachment and detachment method.
Figure 10:
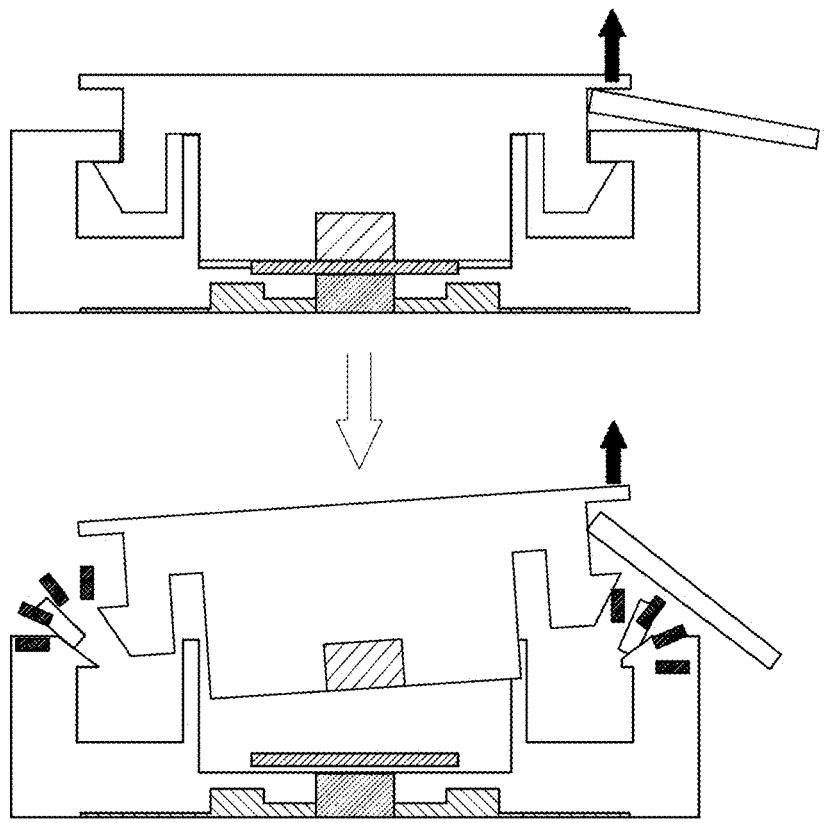
FIG. 10 is a cross-sectional view showing a configuration for attaching and detaching an insert and a base and an attachment and detachment method.

Referring to FIGS. 6 and 7, the first central channel (110) of the microfluidic device may comprise first cells (111), and a second central channel (210) may comprise second cells (211), third cells (212), and/or hydrogel (213). In some embodiments, the first cells (111) are attached to the upper surface of the porous membrane (300) to be cultured, the second cells (211) may be attached to the lower surface of the porous membrane (300) to be cultured, and the third cells (212) may be 3D cultured inside the hydrogel (213).

Referring to FIGS. 8 to 10 and FIG. 18, the base (200) of the microfluidic device comprises an insert insertion groove (201) into which the insert (100) is capable of being inserted, so that the insert (100) can be detachable from the base (200). In addition, the insert (100) comprises a first fastening head (101), the base (200) comprises a second fastening head (202), and the first fastening head (101) and the second fastening head (202) are hooked to each other so that the insert (100) and the base (200) can be attached and detached by a snap fit.

Figure 12:
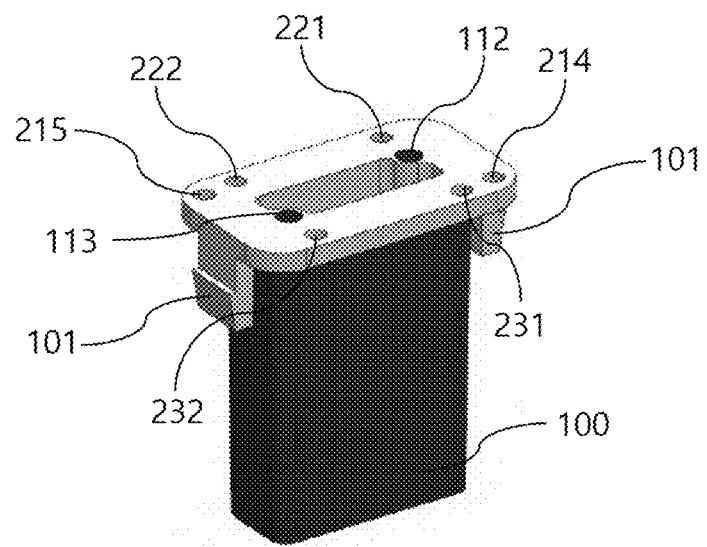
FIG. 12 is a perspective view of an insert.
Figure 13:
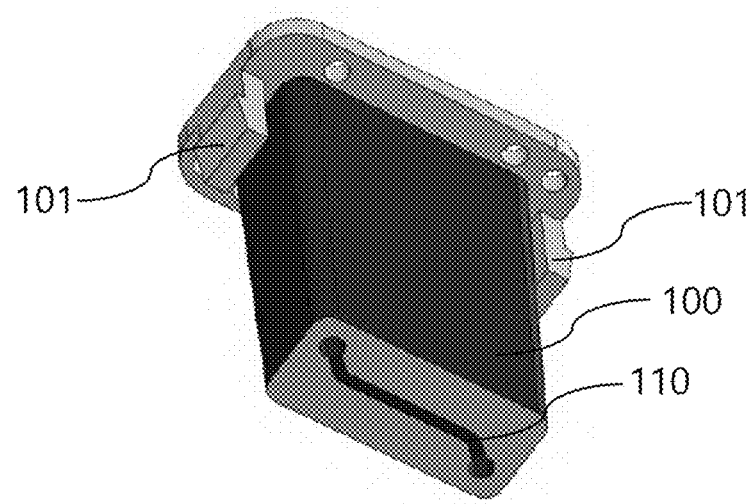
FIG. 13 is a perspective view of an insert.
Figure 14:
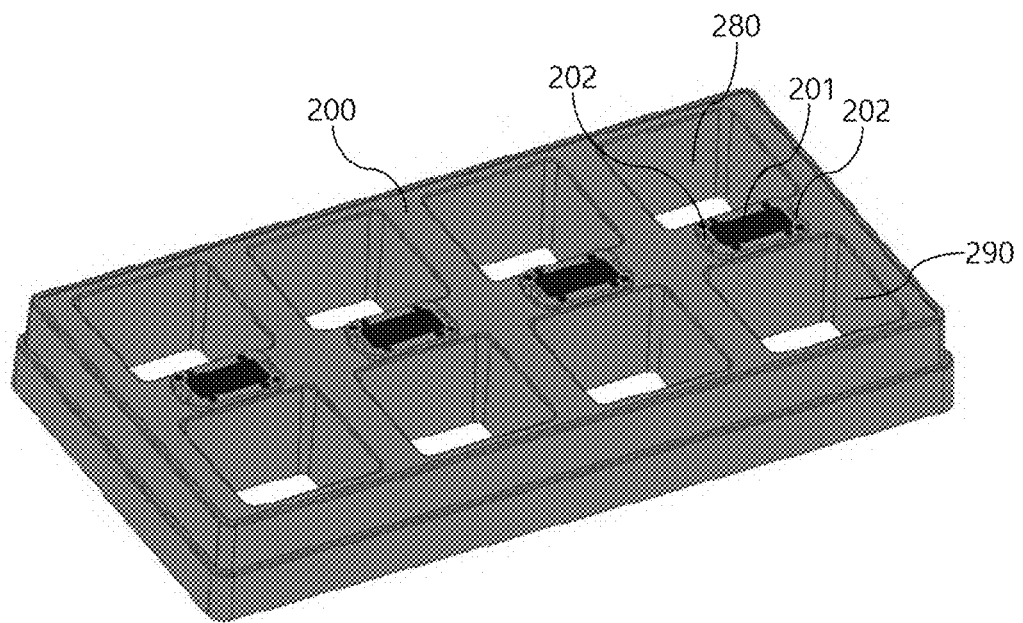
FIG. 14 is a perspective view of a base.
Figure 15:
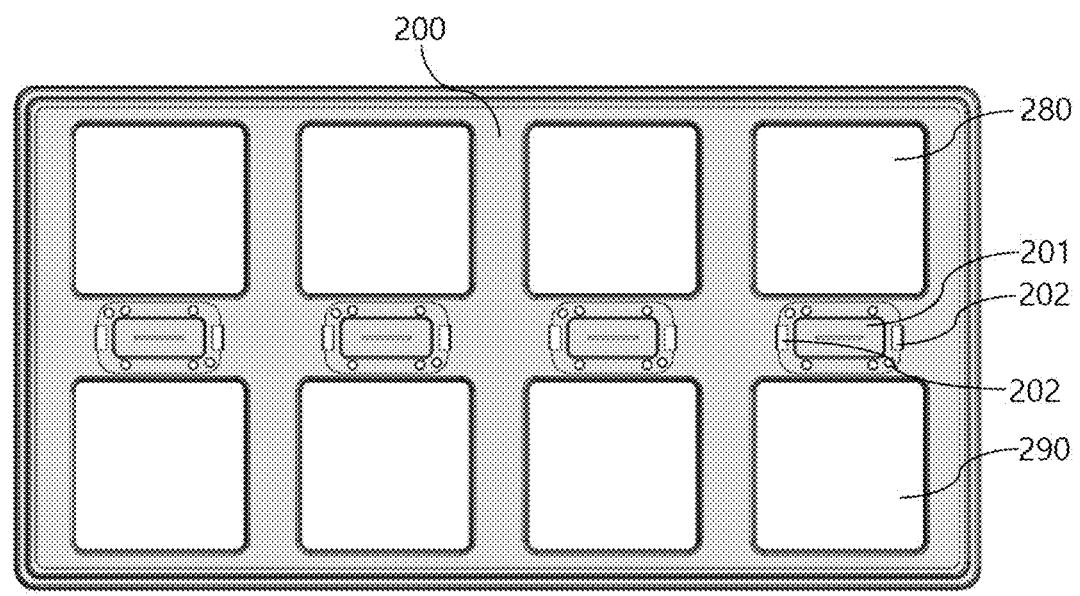
FIG. 15 is a plan view of a base.
Figure 16:
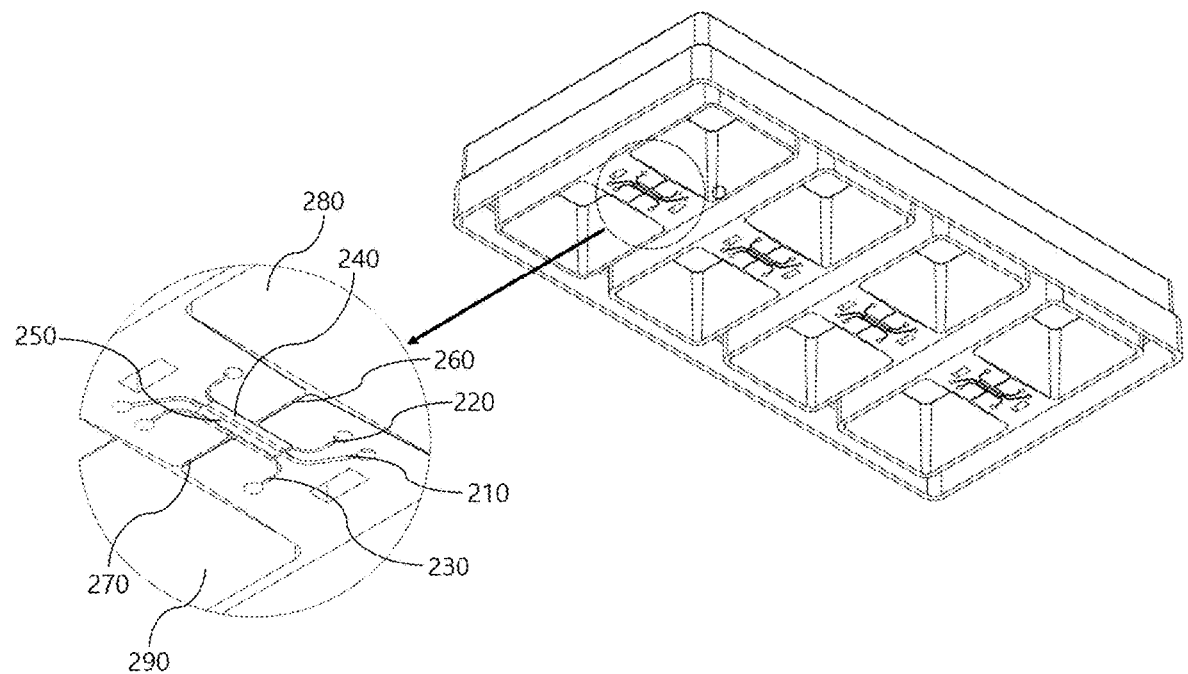
FIG. 16 is a bottom view and an enlarged bottom view of a base.

Referring to FIGS. 12 and 13, the insert (100) of the microfluidic device may comprise an inlet (112) and an outlet (113) of the first central channel, an inlet (214) and an outlet (215) of the second central channel, an inlet (221) and an outlet (222) of the third side channel, and an inlet (231) and an outlet (232) of the fourth side channel. The inlet (112) and the outlet (113) of the first central channel may be connected to the first central channel (110) in a tube shape, and the precise measurement of the TEER value may be possible by inserting the electrode at a certain position and depth through the tube.

Referring to FIGS. 14 to 16 and FIG. 19, the base (200) of the microfluidic device may be a structure to which one or more inserts (100) are detachable. Preferably, it may be a structure to which the four inserts (100) are detachable.

Figure 17:
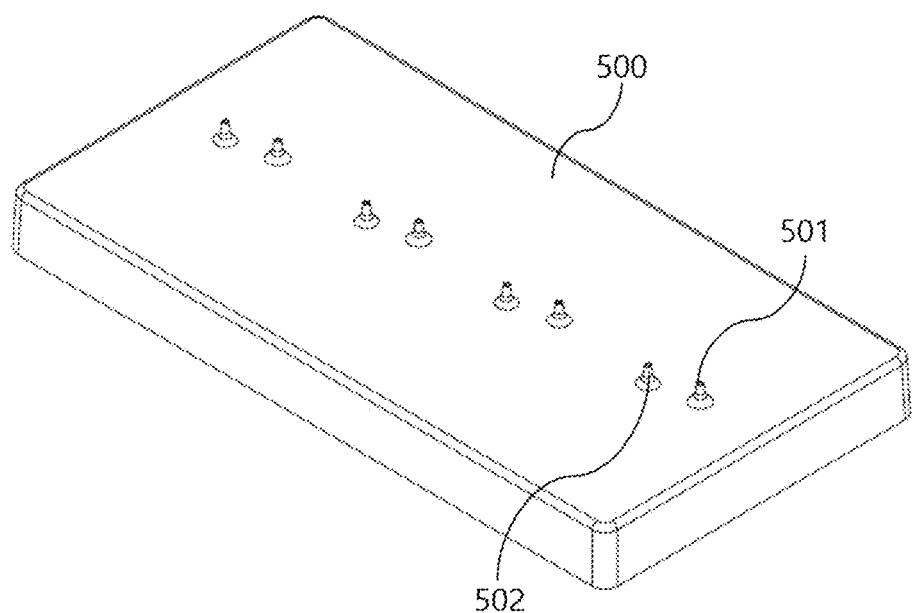
FIG. 17 is a perspective view of a cover.
Figure 18:
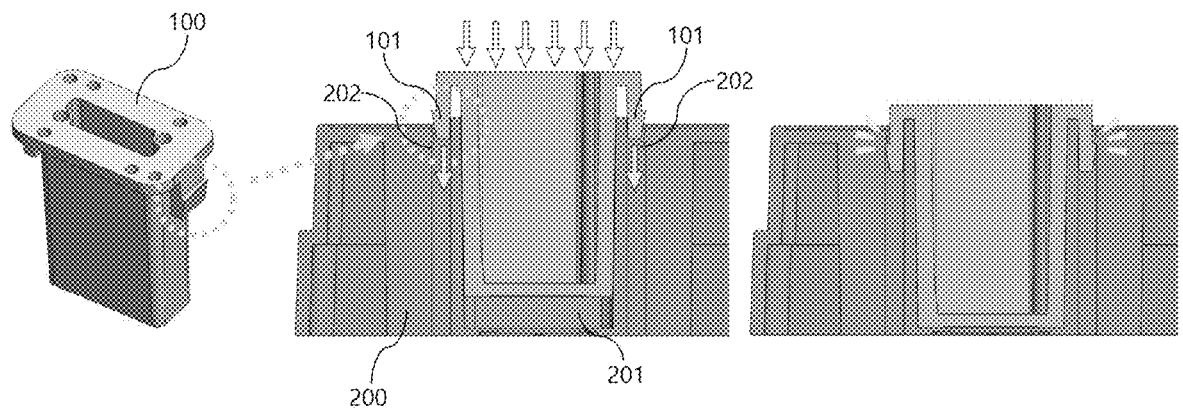
FIG. 18 is a perspective view and a cross-sectional view showing a configuration for attaching and detaching an insert and a base and an attachment and detachment method.
Figure 19:
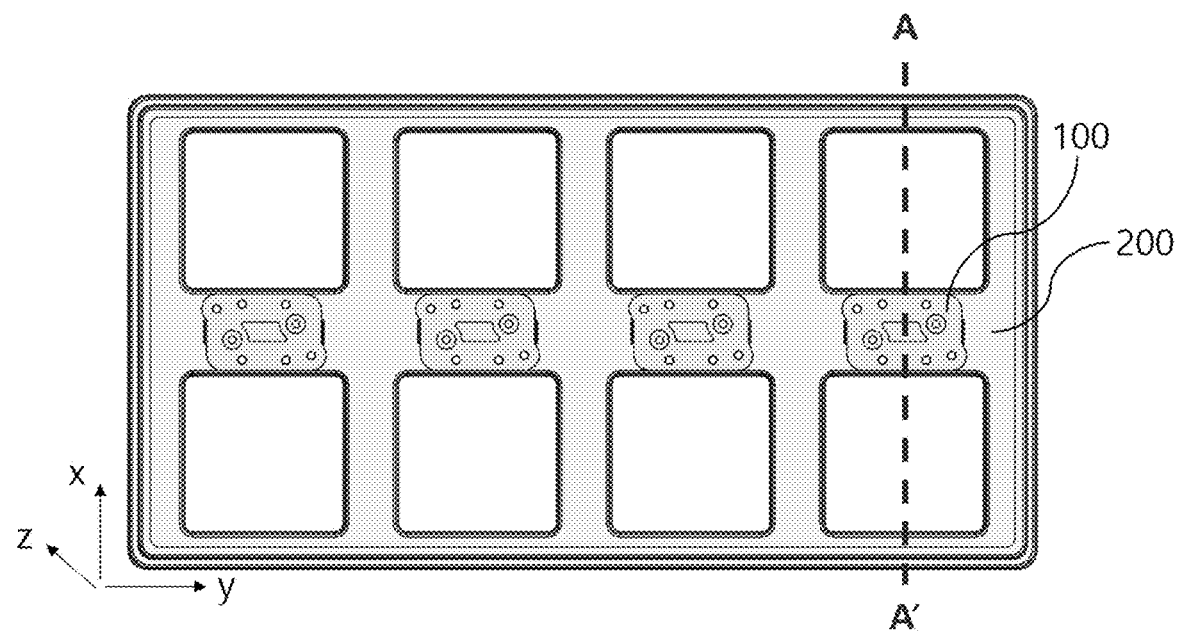
FIG. 19 is a plan view of a microfluidic device in the form in which an insert and a base are attached.
Figure 20:
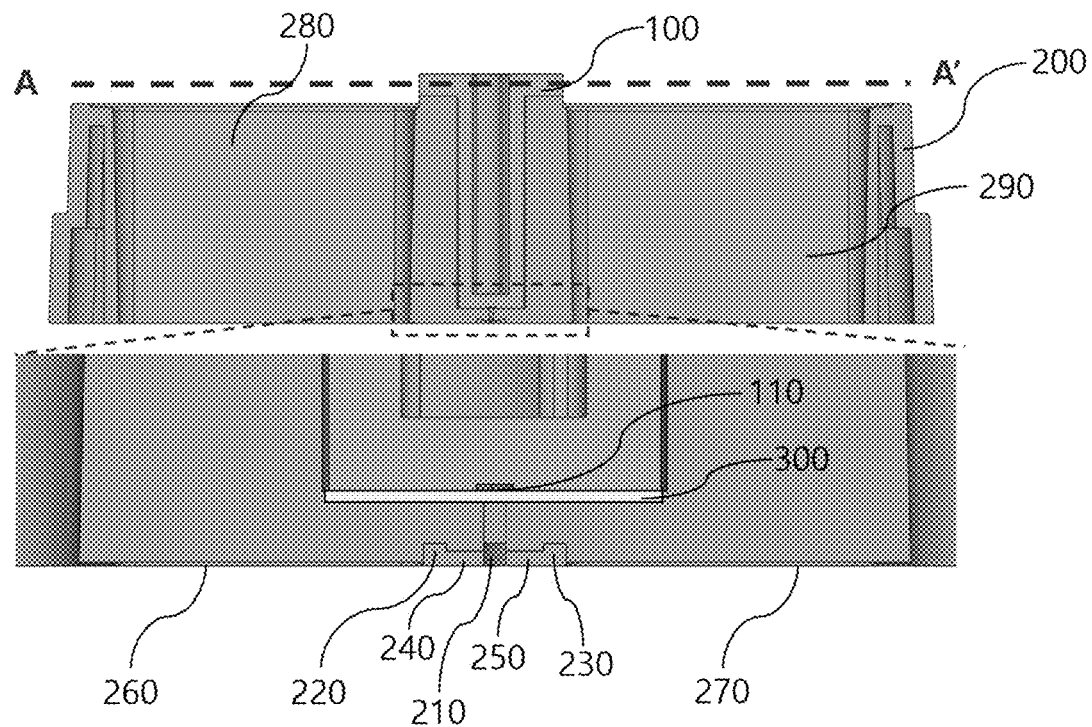
FIG. 20 is an A-A' cross-sectional view and an enlarged cross-sectional view of the microfluidic device of FIG. 19 in the form in which an insert and a base are attached.
Figure 21:
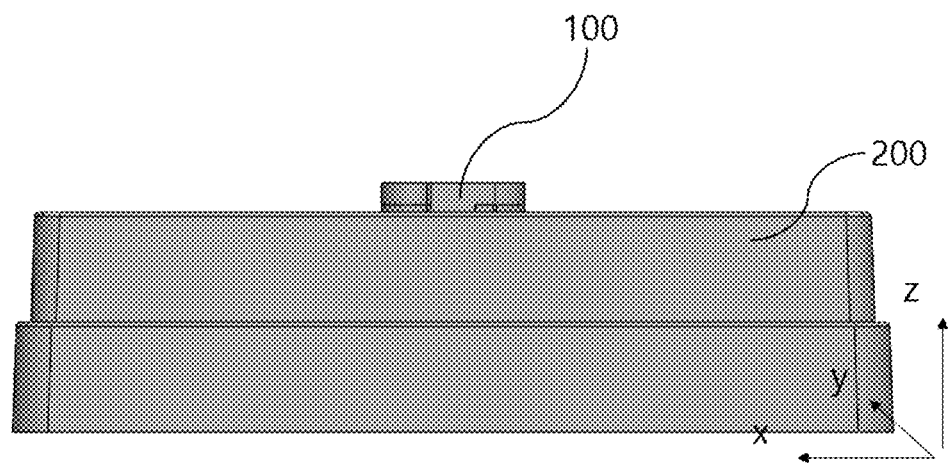
FIG. 21 is a front view of a microfluidic device in the form in which an insert and a base are attached.
Figure 22:
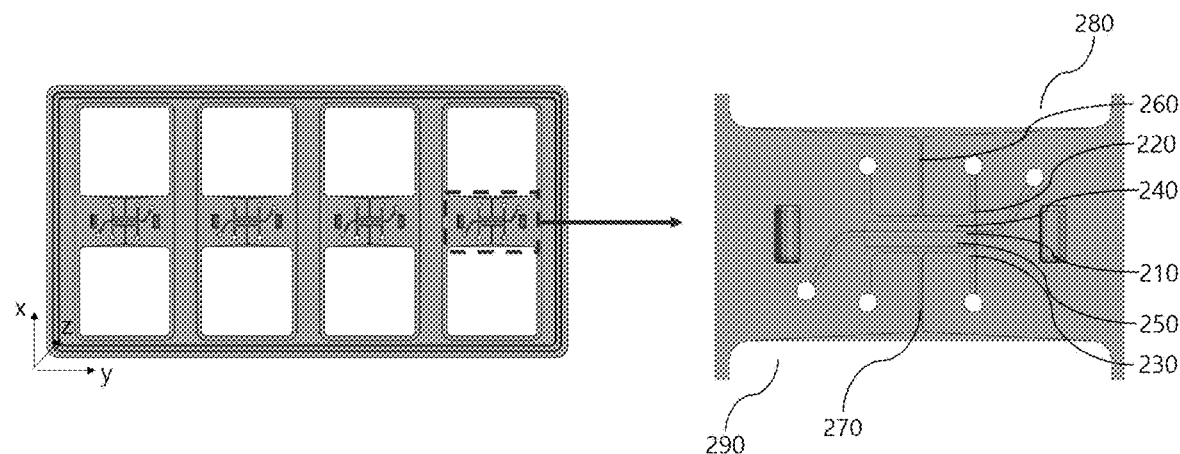
FIG. 22 is a bottom view and an enlarged bottom view of a microfluidic device in the form in which an insert and a base are attached.
Figure 23:
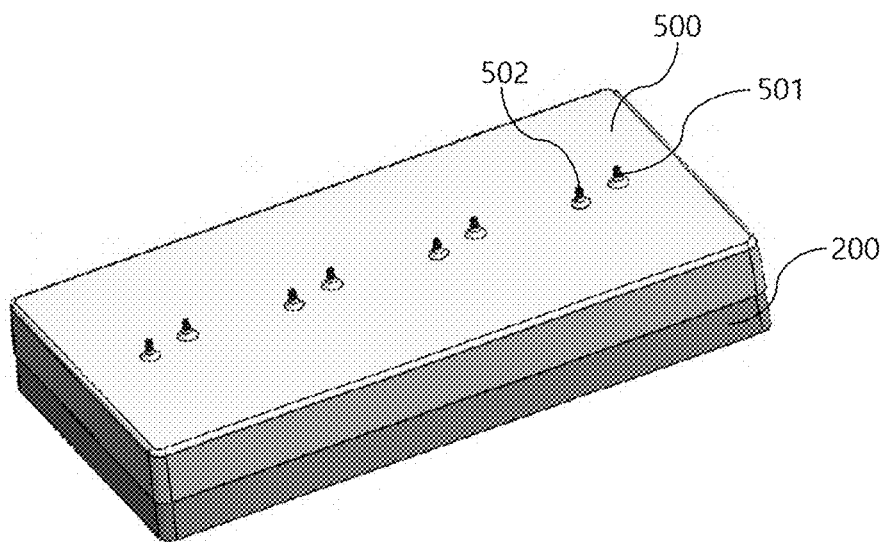
FIG. 23 is a perspective view of a microfluidic device comprising a cover.

Referring to FIGS. 17 and 23, the microfluidic device may comprise a cover (500). The cover (500) may comprise an inlet (501) and an outlet (502) of the first central channel in the cover. The inlet (501) and the outlet (502) of the first central channel in the cover may be in an openable form in order to prevent leakage of fluid.

Figure 24:
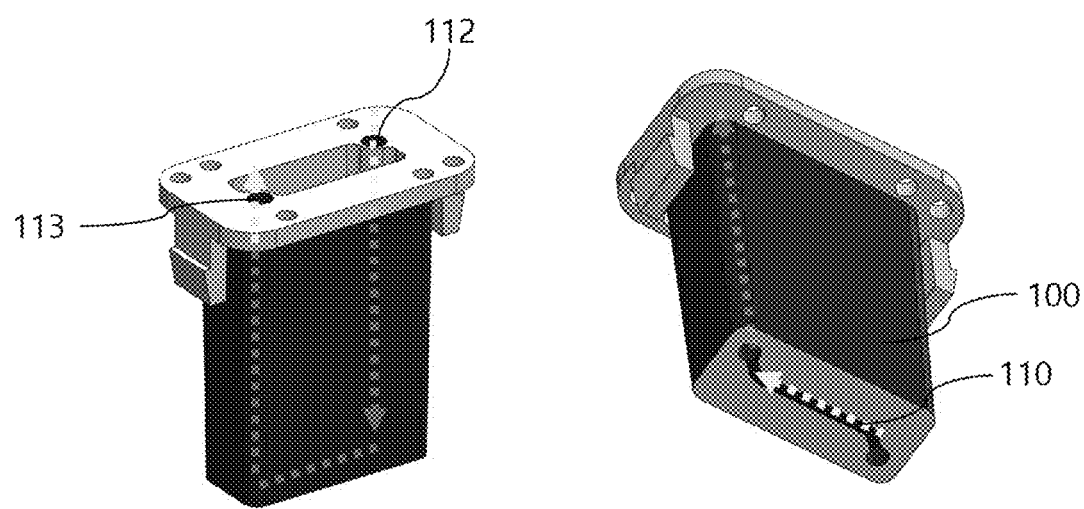
FIG. 24 is a perspective view showing a fluid flow in a microchannel included in an insert.

Referring to FIG. 24, a fluid is injected through the inlet (112) of the first central channel included in the insert (100) of the microfluidic device, and the fluid may be perfused in the direction of the outlet (113) of the first central channel through the first central channel (110).

Figure 11:
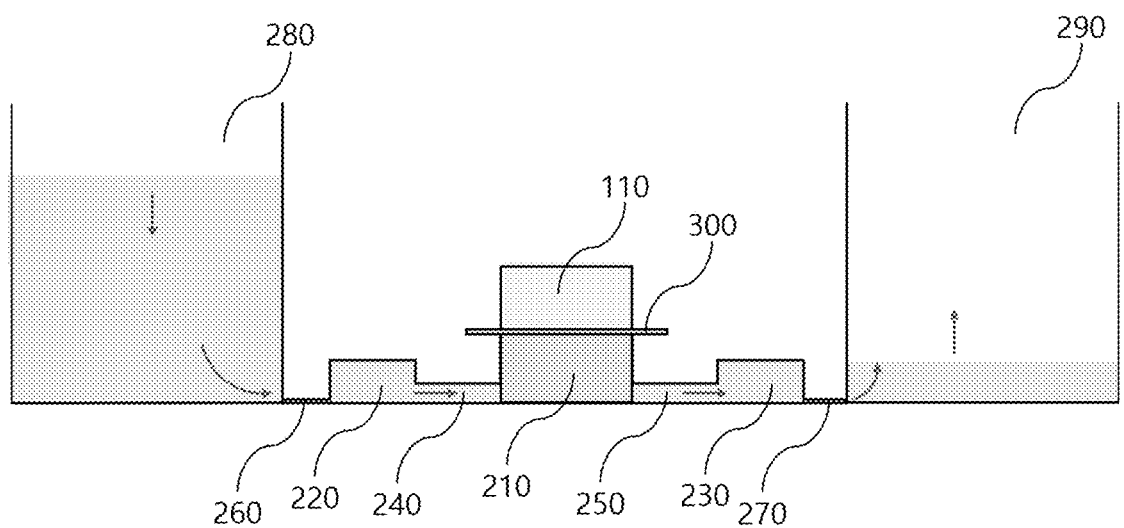
FIG. 11 is a cross-sectional view showing the fluid flow in a base of a microfluidic device.
Figure 25:
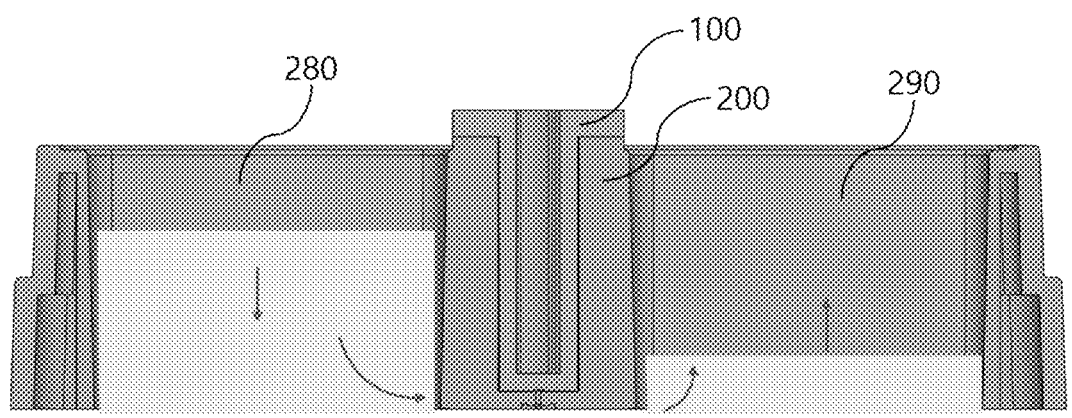
FIG. 25 is a cross-sectional view showing a fluid flow in a microchannel included in a base.

Referring to FIGS. 11 and 25, by injecting a fluid into the first fluid reservoir (280) included in the base (200) of the microfluidic device, the fluid may be sequentially perfused through the third side channel (220), the second central channel (210), the fourth side channel (230), and the second fluid reservoir (290). Preferably, by injecting a fluid into the first fluid reservoir (280) included in the base (200) of the microfluidic device, the fluid may be sequentially perfused through the seventh passage channel (260), the third side channel (220), the fifth passage channel (240), the second central channel (210), the sixth passage channel (250), the fourth side channel (230), the eighth passage channel (270), and the second fluid reservoir (290).

The present disclosure is to be described in more detail through the following examples, but the following examples are for illustrative purposes only and are not intended to limit the scope of the present disclosure.

Example 1: Culture and Viability of Endothelial Cells, Pericytes, and Astrocytes In order to optimize the culture conditions for co-culture of human brain microvascular endothelial cells (HBMEC), human brain vascular pericytes (HBVP), and human astrocytes (HA), the metabolic activity of each cell was compared using the MTS (3-(4,5-dimethylthiazol-2-yl)-5-(3-carboxymethoxyphenyl)-2-(4-sulfophenyl)-2H-tetrazolium) analysis method under six medium conditions. The six medium conditions are as follows, and the glial cell medium (G) refers to 1:1 mixture of astrocyte medium (A) and microglia medium (M).
(i) E: endothelial medium
(ii) A: astrocyte medium
(iii) P: pericyte medium
(iv) M: microglia medium
(v) E+G (E+A+M): 1:1:1 mixture of endothelial medium (E), astrocyte medium (A), and microglia medium (M)
(vi) E+G+P (E+A+M+P): 1:1:1:1 mixture of endothelial medium (E), astrocyte medium (A), microglia medium (M), and pericyte medium (P)

Human brain microvascular endothelial cells (HBMEC), human brain vascular pericytes (HBVP) and human astrocytes (HA) were cultured for 3 days under the six medium conditions, and then CellTiter 96 AQueous One Solution Cell Proliferation Assay (Promega, Madison, WI, USA) was added to each cell. After 4 h of incubation, the optical absorbance of each sample was measured at 490 nm using Cytation 5 plate reader (BioTek, Winooski, VT, USA). Data represent mean±s.d. of n=6 by student t-test (*$p<0.05$, ****$p<0.001$).

Figure 26:
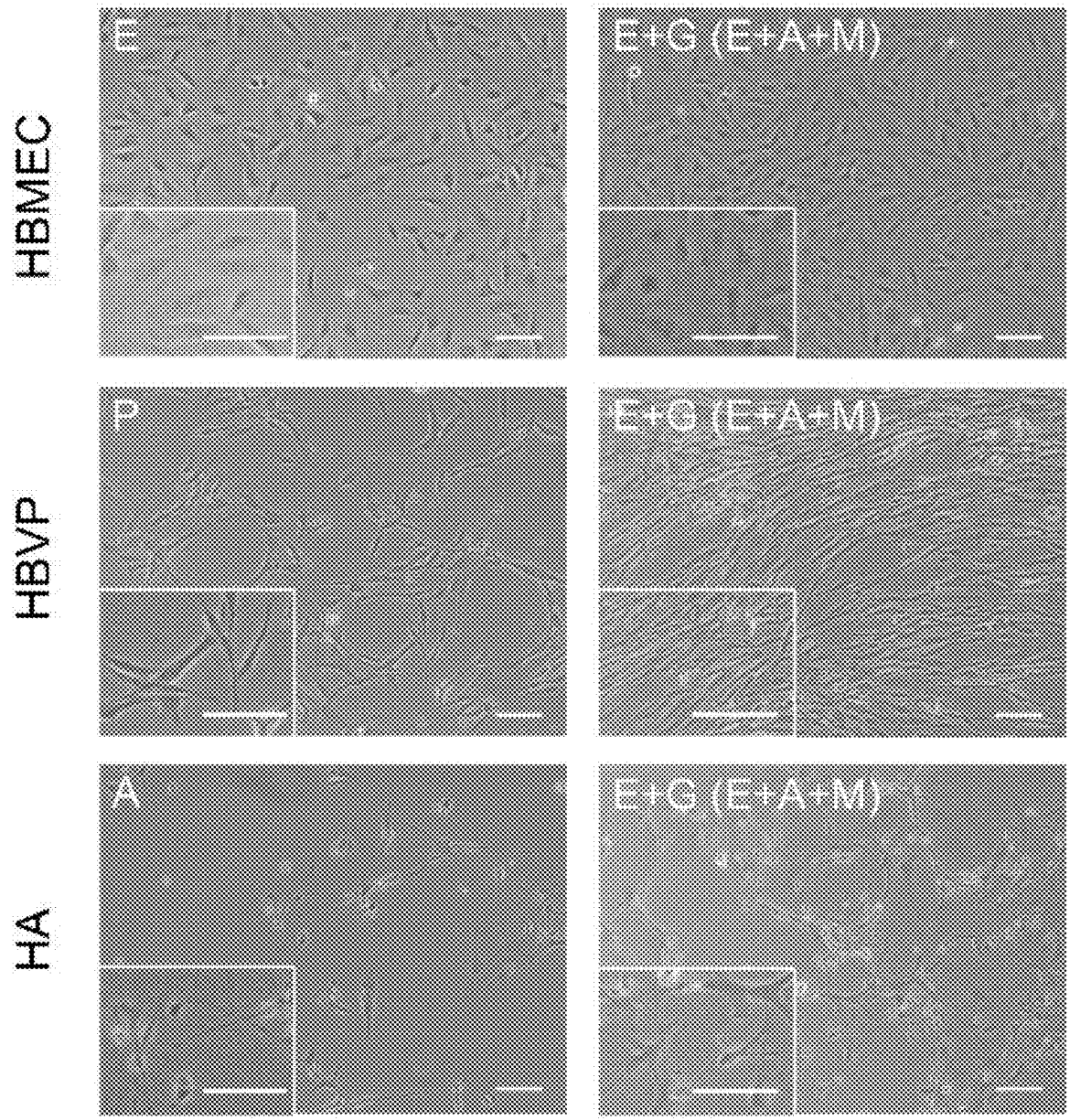
FIG. 26 shows the cell morphology of human brain microvascular endothelial cells (HBMEC), human brain vascular pericytes (HBVP), or human astrocytes (HA) when cultured in endothelial medium (E), pericyte medium (P), or astrocyte medium (A), which is its respective culture medium, and when cultured in E+G (E+A+M) medium, which a mixed medium.

As shown in FIG. 26, it was confirmed that the cell culture of human brain microvascular endothelial cells (HBMEC), human brain vascular pericytes (HBVP), or human astrocytes (HA) was more excellent when cultured in E+G (E+A+M) medium, which a mixed medium, than when cultured in endothelial medium (E), pericyte medium (P), or astrocyte medium (A), which is its respective culture medium.

Figure 27:
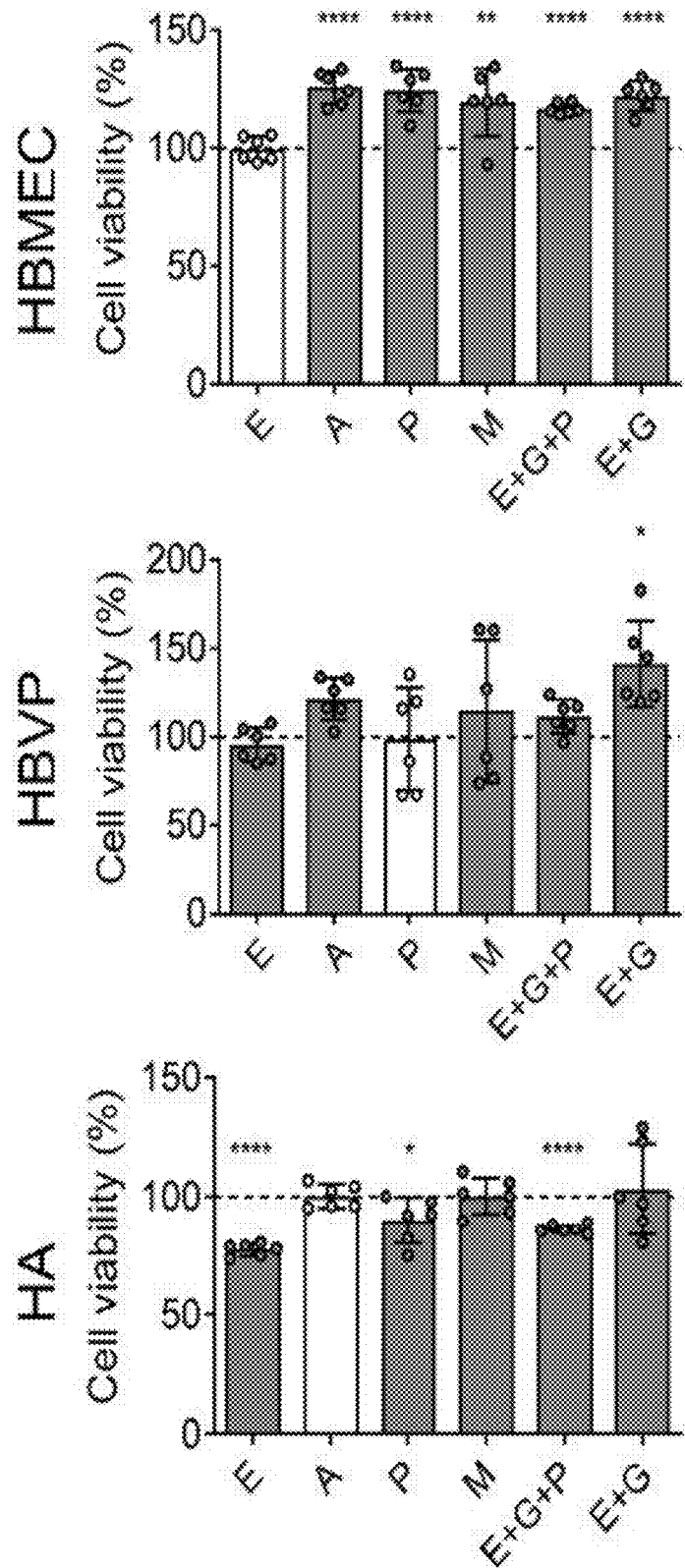
FIG. 27 is a graph showing the cell activity of human brain microvascular endothelial cells (HBMEC), human brain vascular pericytes (HBVP), or human astrocytes (HA) when cultured in endothelial medium (E), astrocyte medium (A), pericyte medium (P), microglia medium (M), E+G+P (E+A+M+P) medium, or E+G (E+A+M) medium, respectively.
Figure 28:
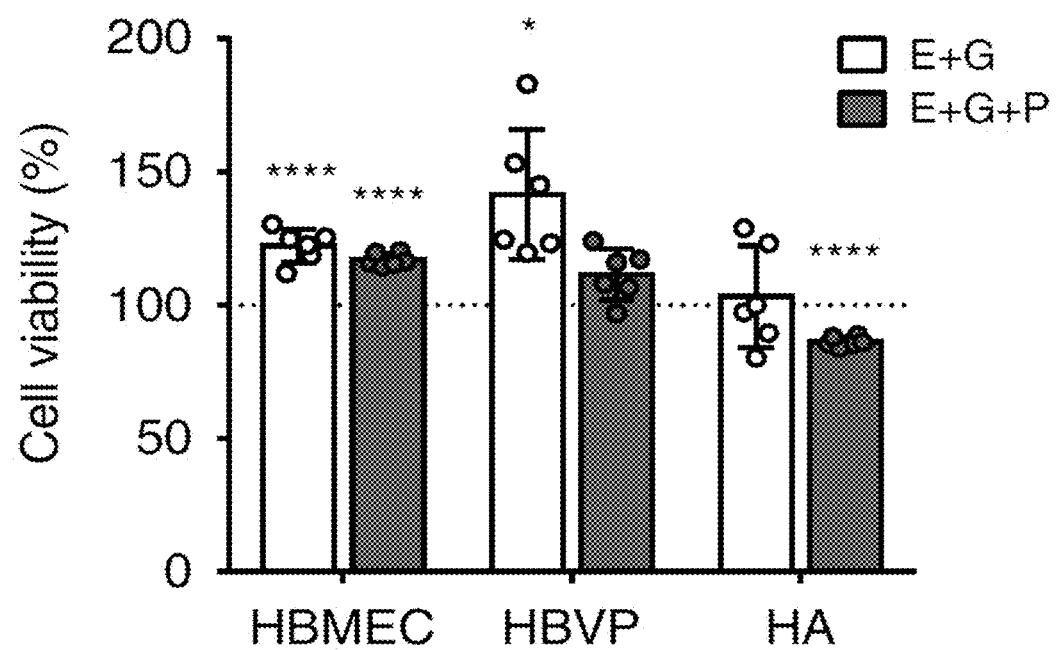
FIG. 28 is a graph showing the cell activity of human brain microvascular endothelial cells (HBMEC), human brain vascular pericytes (HBVP), or human astrocytes (HA) when cultured in E+G (E+A+M) medium or E+G+P (E+A+M+P) medium, which is a mixed medium, respectively.

In addition, as shown in FIGS. 27 and 28, it was confirmed that both human brain microvascular endothelial cells (HBMEC) and human brain vascular pericytes (HBVP) had excellent viability in E+G and E+G+P media, and human astrocytes (HA) had excellent viability in E+G medium.

According to the above experiment results, in the following examples, cell culture was carried out using E+G (E+A+M) medium, which is 1:1:1 mixture of endothelial medium (E), astrocyte medium (A), and microglia medium (M).

Example 2: Preparation of Microfluidic Device Simulating Blood-Brain Barrier (BBB)

Using the assembled microfluidic device, a microfluidic device simulating blood-brain barrier (BBB) was prepared in the following manner.

Figure 29:
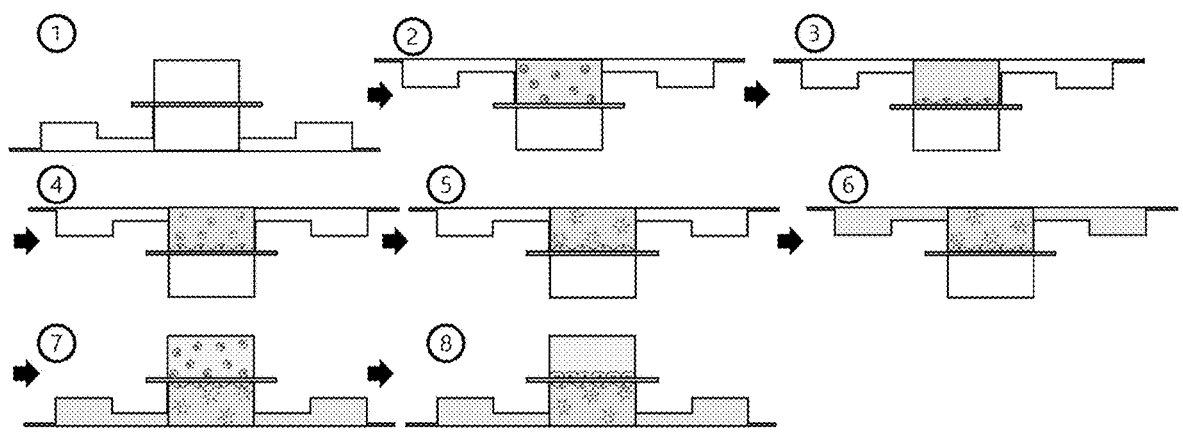
FIG. 29 is a schematic diagram showing a method of culturing cells in a microfluidic device.

As shown in FIG. 29, 10 µl of human brain vascular pericytes (HBVP) at a concentration of $10^6$ to $10^7$ cells/ml was injected into the second central channel, and incubated for 1 h so that the pericytes could be evenly attached to the surface of the porous membrane by inverting the microfluidic device, and then the culture solution was replaced. After at least 6 h, 10 µl of human astrocytes (HA) at a concentration of $10^5$ to $10^6$ cells/ml embedded in Matrigel was injected into the second central channel. The culture was carried out for 1 h so that Matrigel was hardened, and the culture solution was injected into the third side channel and the fourth side channel, and then the culture was carried out for at least 6 h. The microfluidic device was inverted again, and then 15 µl of human brain microvascular endothelial cells (HBMEC) at a concentration of $7\times10^7$ cells/ml was injected into the first central channel and cultured for 1 h, and then the culture solution was replaced.

Example 3: Confirmation of Expression Level of Blood-Brain Barrier (BBB) Specific Protein In order to test a three-dimensional tissue barrier function of the microfluidic device simulating blood-brain barrier (BBB) prepared in Example 2 comprising human brain microvascular endothelial cells (HBMEC), human brain vascular pericytes (HBVP) and human astrocytes (HA), the expression level of the blood-brain barrier specific protein was confirmed through qRT-PCR analysis. For comparison, the protein expression was confirmed together when only human brain microvascular endothelial cells (HBMEC) were single-cultured.

RNA from HBMECs and HAs were isolated and collected using the RNeasy Mini kit (Qiagen GmBH, Hilden, Germany), and the amount of collected RNA samples were measured by Cytation 5 plate reader. 800 ng of HBMEC RNA and 280 ng of HA RNA were reverse-transcribed into cDNA with T100 Thermal Cycler (Bio-Rad, Hercules, CA, USA) using High-capacity cDNA Reverse Transcription kit (Applied Biosystems, Foster City, CA, USA). To analyze endothelial specific gene expressions in HBMECs (n=3), microfluidic qRT-PCR was performed with Flex Six IFC (Fluidigm, South San Francisco, CA, USA) using the Fluidigm Biomark system (Fluidigm). The target genes were assessed using commercially available primers, the primers used in the experiment are shown in Table 1 below.

measured. For comparison, the TEER value was confirmed together when a single culture of only human brain microvascular endothelial cells (HBMEC) was carried out. TEER (Transendothelial electrical resistance) is a method of measuring the electrical resistance of a cell layer using Ohm's law, and is one of the factors indicating how the cell barrier made of the cell layer functions well. The stronger the cell layers bind to each other, the stronger the expression of the junction protein, which forms the binding between cells, and the paracellular material transport is limited, and thus the electrical resistance value is increased. The human blood-brain barrier is a barrier in which the material transport is extremely limited, and its TEER value is estimated to be 5000 $\Omega \cdot cm^2$ [Lauschke K, Frederiksen L, Hall V J (2017) Paving the way toward complex blood-brain barrier models using pluripotent stem cells. Stem Cells Dev 26(12):857-874], and the rat blood-brain barrier was measured to be

TABLE 1

| Experiment | Gene Symbol | Gene Name | TaqMan Assay ID # |
|---|---|---|---|
| Control HBMEC Fluidigm | GAPDH | Glyceraldehyde-3-phosphate dehydrogenase | Hs02786624_g1 |
| | vWF | von Willebrand factor | Hs01109446_m1 |
| | SELE | Selectin E | Hs00174057_m1 |
| | PECAM1 | Platelet and endothelial cell adhesion molecule 1 | Hs01065279_m1 |
| | VECAD | Cadherin 5 (CDH5) | Hs00901465_m1 |
| | OCLN | Occludin | Hs00170162_m1 |
| | ZO-1 | Tight junction protein 1 (TJP1) | Hs01551861_m1 |
| | CAT1 | Solute carrier family 7 member 1 (SLC7A1) | Hs00931450_m1 |
| | LAT1 | Solute carrier family 7 member 5 (SLC7A5) | Hs00185826_m1 |
| | OCT1 | Solute carrier family 22 member 1 (SLC22A1) | Hs00427552_m1 |
| | GLUT1 | Solute carrier family 2 member 1 (SLC2A1) | Hs00892681_m1 |
| | CERP | ATP binding cassette subfamily A member 1 (ABCA1) | Hs01059137_m1 |
| | P-GP | ATP binding cassette subfamily B member 1 (ABCB1) | Hs00184500_m1 |
| | MRP1 | ATP binding cassette subfamily C member 1 (ABCC1) | Hs01561483_m1 |
| | LRP1 | LDL receptor related protein 1 | Hs00233856_m1 |
| | AGER | Advanced glycosylation end-product receptor | Hs00542584_g1 |
| | ICAM1 | Intercellular adhesion molecule 1 | Hs00164932_m1 |
| | VCAMI | Vascular cell adhesion molecule 1 | Hs01003372_m1 |

Figure 30:
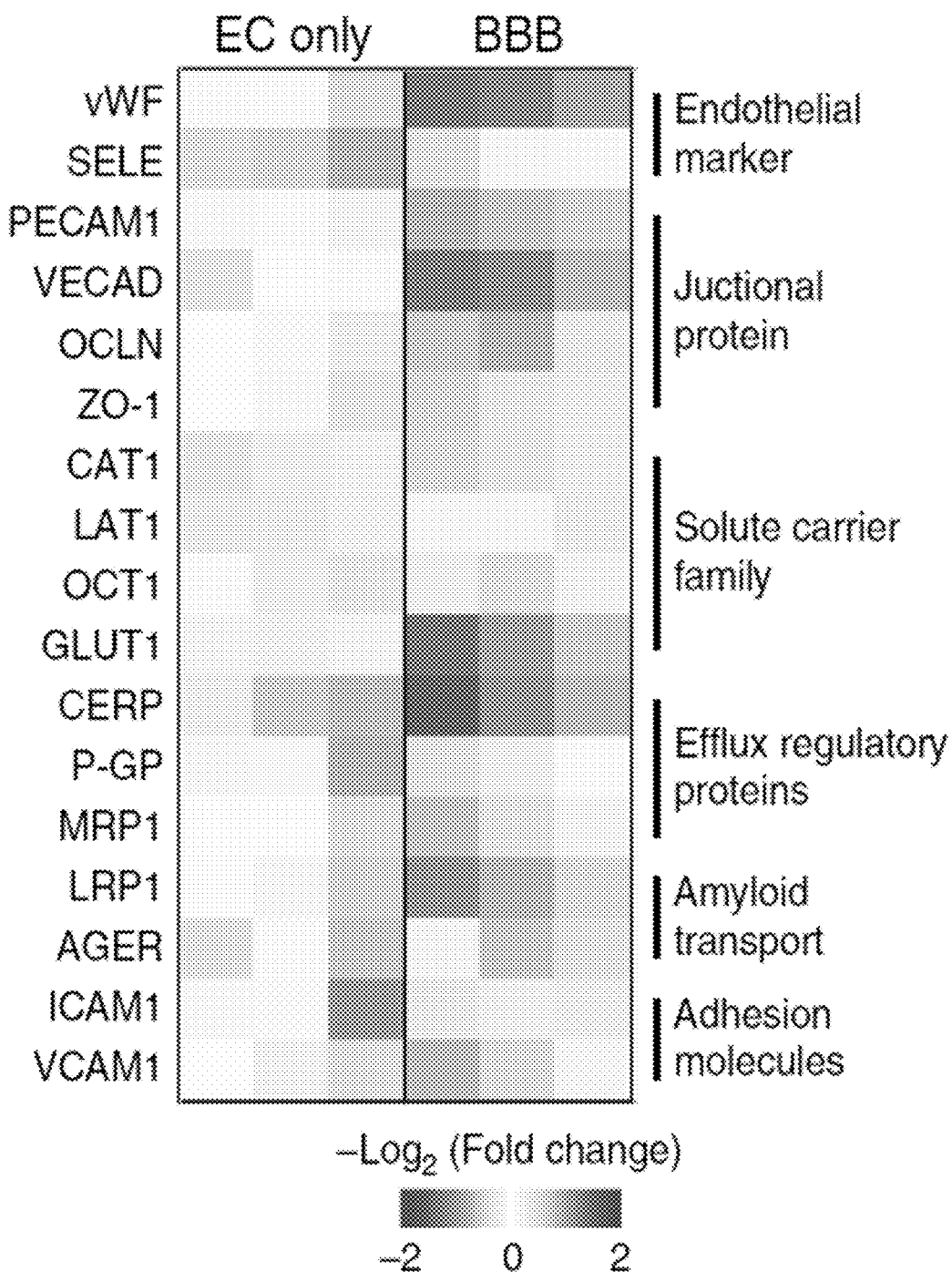
FIG. 30 is a heat map showing the results of RT-qPCR showing the expression level of blood-brain barrier specific proteins in a single culture of human brain microvascular endothelial cells (HBMEC) and in a microfluidic device simulating blood-brain barrier (BBB) (n=3).
Figure 31:
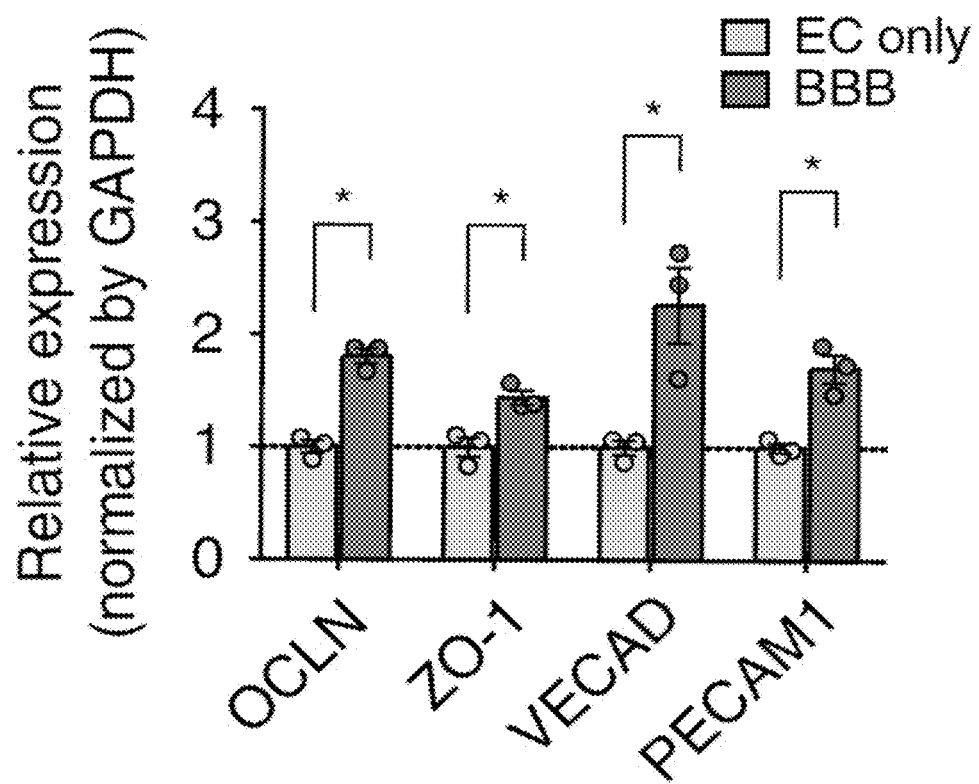
FIG. 31 is a graph showing the gene expression level of blood-brain barrier specific junctional proteins in a single culture of human brain microvascular endothelial cells (HBMEC) and in a microfluidic device simulating blood-brain barrier (BBB) (n=3, *p<0.05 by student t-test).
Figure 32:
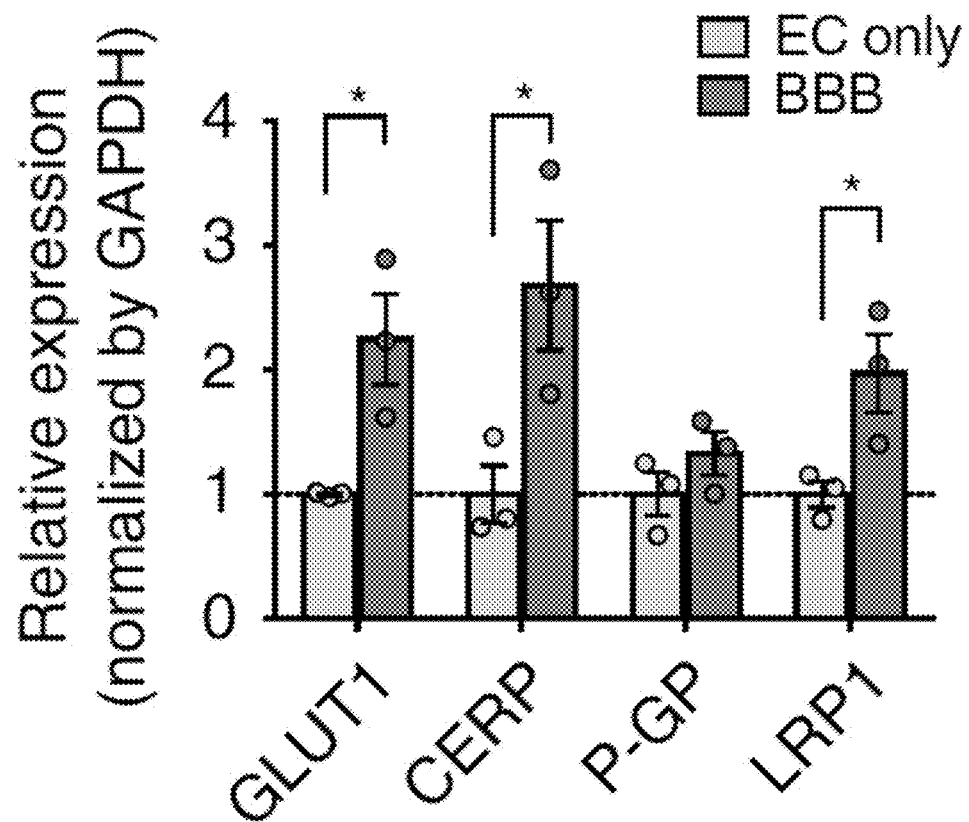
FIG. 32 is a graph showing the gene expression level of blood-brain barrier specific receptor proteins in a single culture of human brain microvascular endothelial cells (HBMEC) and in a microfluidic device simulating blood-brain barrier (BBB) (n=3, *p<0.05 by student t-test).

As shown in FIG. 30, it was confirmed that the expression of all blood-brain barrier (BBB) specific proteins used in the evaluation, including proteins that control the regulation of junctional formation, carrier-mediated transport, active efflux or amyloid beta (Aβ) transport in the BBB, was increased in a microfluidic device simulating the BBB comprising human brain microvascular endothelial cells (HBMEC), human brain vascular pericytes (HBVP) and human astrocytes (HA) compared to when a single culture of only human brain microvascular endothelial cells (HBMEC) was carried out. In particular, as shown in FIGS. 31 and 32, it was confirmed that the gene expression level of blood-brain barrier specific junctional proteins and receptor proteins was remarkably increased compared to when a single culture of endothelial cells was carried out.

Example 4: Comparison of TEER (Transendothelial Electrical Resistance) Value

In order to test a three-dimensional tissue barrier function of the microfluidic device simulating blood-brain barrier (BBB) prepared in Example 2 comprising human brain microvascular endothelial cells (HBMEC), human brain vascular pericytes (HBVP) and human astrocytes (HA), the TEER (Transendothelial electrical resistance) value was 5900 $\Omega \cdot cm^2$. [Butt A M, Jones H C, Abbott N J (1990) Electrical resistance across the blood-brain barrier in anaesthetized rats: a developmental study. J Physiol 429:47-62]

The TEER value of a barrier layer of the microfluidic device simulating blood-brain barrier (BBB) and a single culture layer of human brain microvascular endothelial cells (HBMEC) was measured using a custom electrode adapter made with Rj11 plug and Ag, Ag/AgCl electrode wires (381 μm in diameter and 3 cm in length, A-M Systems, Sequim, WA, USA) connected to EVOM2 volt-ohmmeter (Word Precision Instruments, Sarasota, FL, USA) which generates a constant 10 μA of AC current at 12.5 Hz. To reduce background resistance and error, the electrode wires were placed in a tygon tubing (1/32"ID×3/32"OD, Cole-Parmer, Vernon Hills, IL, USA) filled with culture medium and inserted into the channels. After 1 min of stabilization, 5 multiple readings were averaged for each device. To calculate TEER, the measurements in the absence of the cells were subtracted from the resistance of each device, and then the values were multiplied by the surface area of layer.

Figure 33:
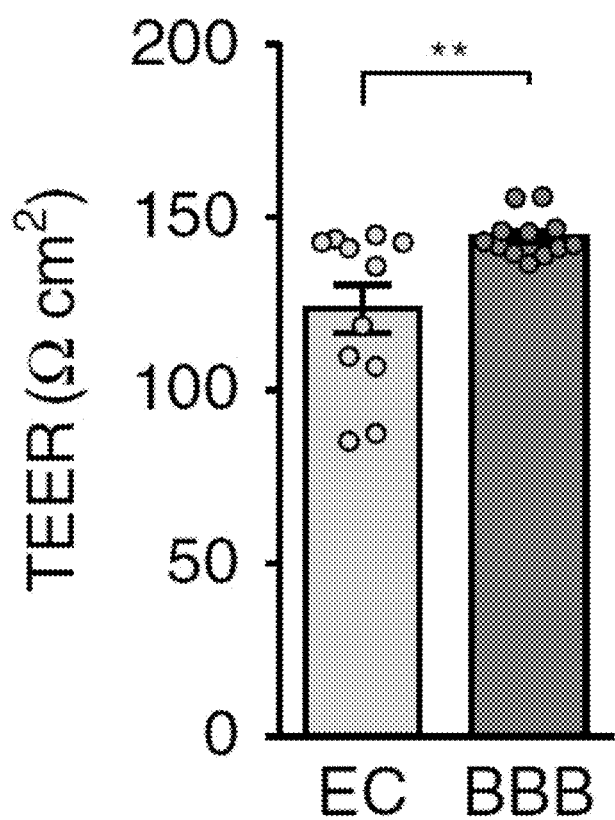
FIG. 33 is a graph showing the TEER value measured in a single culture of human brain microvascular endothelial cells (HBMEC) and in a microfluidic device simulating blood-brain barrier (BBB) (n=11 (EC), n=12 (BBB), **p<0.01 by student t-test).

As shown in FIG. 33, the TEER value in the microfluidic device simulating blood-brain barrier (BBB) was higher compared to when a single culture of human brain microvascular endothelial cells (HBMEC) was carried out, and thus it was confirmed that the blood-brain barrier (BBB)

could be better simulated when human brain microvascular endothelial cells (HBMEC), human brain vascular pericytes (HBVP) and human astrocytes (HA) were cultured together.

Example 5: Comparison of TEER Value According to the Difference in Shear Stress of Blood Simulation Flow In order to test the difference in a three-dimensional tissue barrier function according to the shear stress of blood simulation flow applied to the first central channel of the microfluidic device simulating blood-brain barrier (BBB) prepared in Example 2, each TEER (Transendothelial electrical resistance) value was measured by the same method as in Example 4 when no shear stress was applied to the first central channel, when a shear stress of 0.4 dyne cm$^{-2}$ was applied, and when a shear stress of 4 dyne cm$^{-2}$ was applied.

Figure 34:
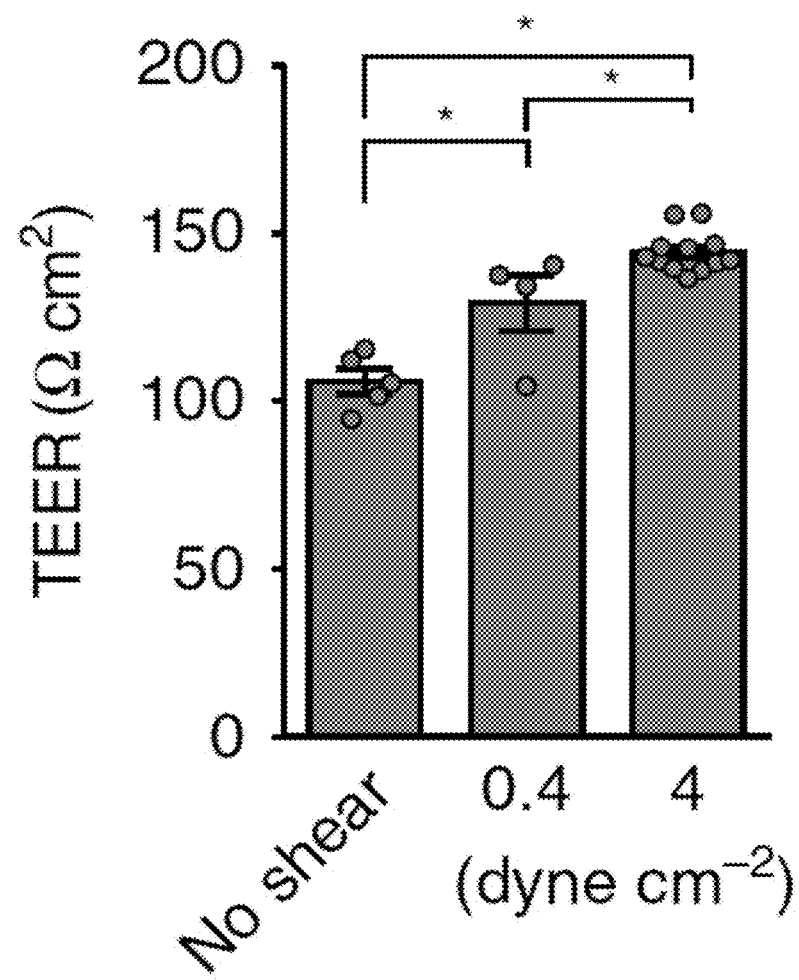
FIG. 34 is a graph showing the TEER value according to the difference in shear stress of the blood simulation flow measured in a microfluidic device simulating blood-brain barrier (BBB) (n=5 (No shear), n=4 (0.4 dyne cm$^{-2}$), n=12 (4 dyne cm$^{-2}$), *p<0.05 by student t-test).

As a result, as shown in FIG. 34, it was confirmed that when a shear stress of 4 dyne cm$^{-2}$ was applied, when a shear stress of 0.4 dyne cm$^{-2}$ was applied, and when no shear stress was applied, the TEER values were sequentially high.

Example 6: Comparison of Permeability Coefficient

In order to test a three-dimensional tissue barrier function of the microfluidic device simulating blood-brain barrier (BBB) prepared in Example 2 comprising human brain microvascular endothelial cells (HBMEC), human brain vascular pericytes (HBVP) and human astrocytes (HA), the permeability coefficient was measured from the diffusion of 4 kDa and 40 kDa FITC-dextran. For comparison, the permeability coefficient was confirmed together when cells were not cultured and when only human brain microvascular endothelial cells (HBMEC) were single-cultured.

The cells in the microfluidic device were cultured for 60 h, and then the culture medium containing FITC-dextran (Sigma-Aldrich) of 4 kDa or 40 kDa at a concentration of 500 μg/mL was injected into the first central channel of the microfluidic device at a flow rate of 16 μL/min using PhD Ultra syringe pump (Harvard Apparatus). Simultaneously, culture medium from one side channel was sampled at 4 μL/min with a syringe pump for 1 h. Fluorescence intensities of 500 μg/mL of FITC-dextran solution and the sampled solutions are measured using a Cytation 5 plate reader (n=4). The dextran concentrations (C) in the solutions were calculated with the measured fluorescence intensity values using a standard calibration curve, permeability coefficients (P) were calculated using the following equation.

$$P = V \frac{\frac{dC}{dt}}{\Delta C}$$

(V: the volume of the sampled solution, $\frac{dC}{dt}$

: the concentration difference in the channel in the base over time, ΔC: the concentration difference across the barrier)

Figure 35:
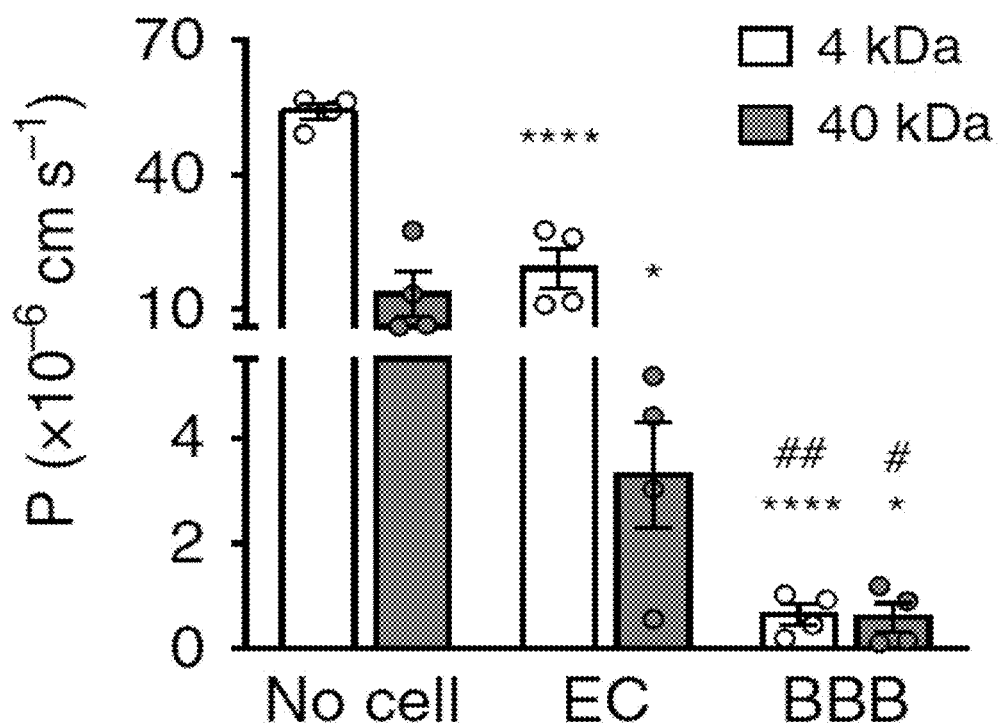
FIG. 35 is a graph showing the permeability coefficient (P) measured in a cell-free culture, in a single culture of human brain microvascular endothelial cells (HBMEC), and in a microfluidic device simulating blood-brain barrier (BBB) (n=4, *p<0.05, ****p<0.001 vs. No cell, #p<0.05, ##p<0.01 vs. EC, student t-test).

As shown in FIG. 35, it was confirmed that the three-dimensional tissue barrier of the microfluidic device simulating blood-brain barrier (BBB) comprising human brain microvascular endothelial cells (HBMEC), human brain vascular pericytes (HBVP) and human astrocytes (HA) exhibited remarkably low permeability coefficient at both 4 kDa and 40 kDa compared to when the cells were not cultured, and when only human brain microvascular endothelial cells (HBMEC) were single-cultured. That is, it was confirmed that when all three cells were cultured, they performed the function most similar to the blood-brain barrier.

Example 7: Comparison of Structure and Function of Astrocytes According to Culture Method In the astrocyte culture in the second central channel of the microfluidic device simulating blood-brain barrier (BBB) prepared in Example 2 comprising human brain microvascular endothelial cells (HBMEC), human brain vascular pericytes (HBVP) and human astrocytes (HA), the difference between 2D culture and 3D culture was compared. Preserving the morphological and physiological properties of healthy astrocytes plays an important role in simulating the function of the blood-brain barrier.

In order to compare the structure and function of human astrocytes (HA) in 2D and 3D cultures, HAs were seeded at a density of 1×10$^6$ cells/mL in Matrigel (Growth factor-reduced; Corning, NY, USA) coated 24-wells and in 3D Matrigel (5 mg/mL). After 1 day of culture, cells were stimulated with 1 ng/mL or 10 ng/mL of recombinant human interleukin-1-beta (IL-1β; Gibco, Grand Island, NY, USA) and incubated for another 20 h for analysis.

Comparison of Structure of Astrocytes According to Culture Method

Figure 36:
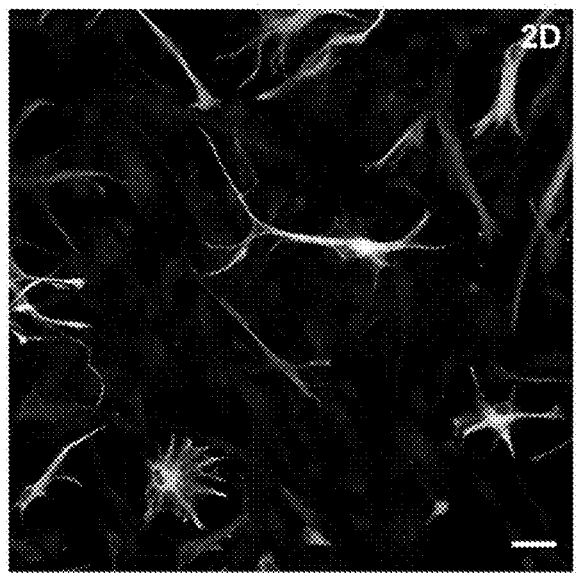
FIG. 36 shows the morphology of human astrocytes (HA) cultured on the 2D Matrigel-coated surface and the morphology of human astrocytes (HA) cultured inside the 3D Matrigel.
Figure 36:
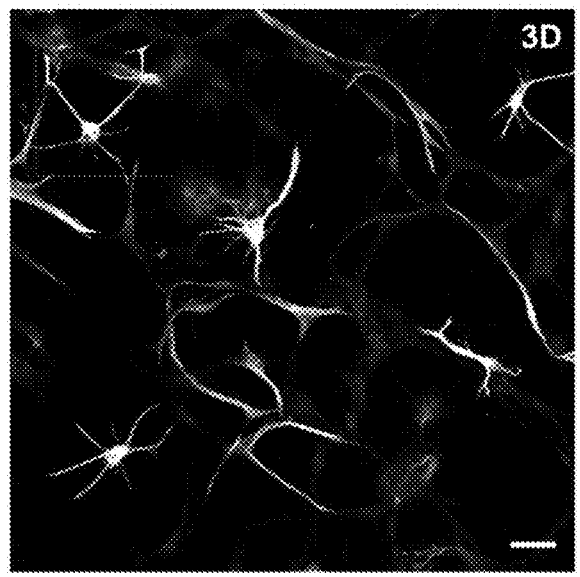
Figure 37:
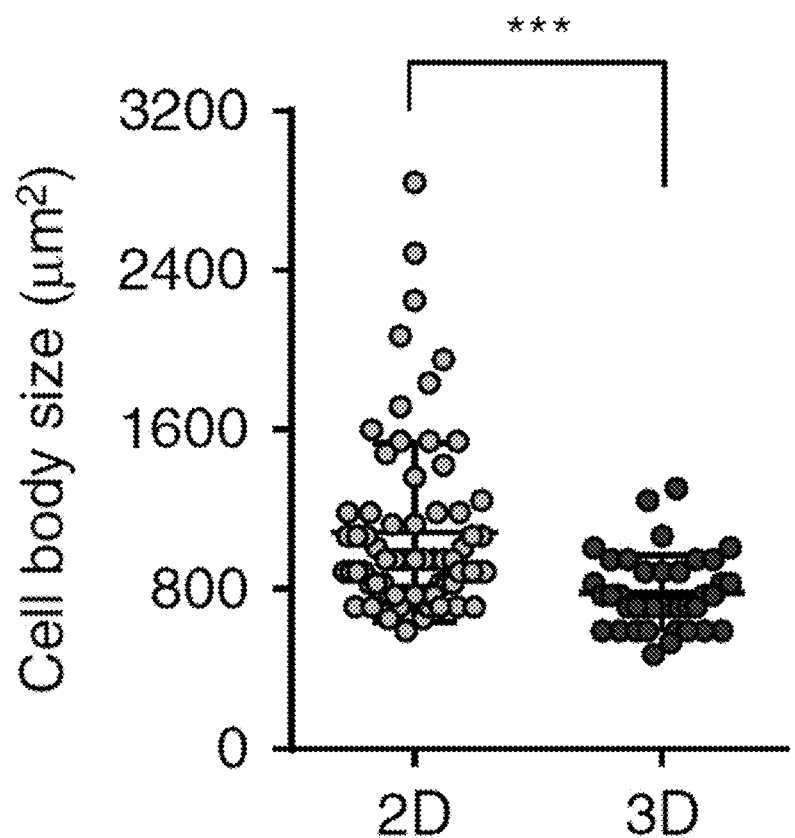
FIG. 37 is a graph comparing the cell body size of human astrocytes (HA) cultured on the 2D Matrigel-coated surface and inside the 3D Matrigel.
Figure 38:
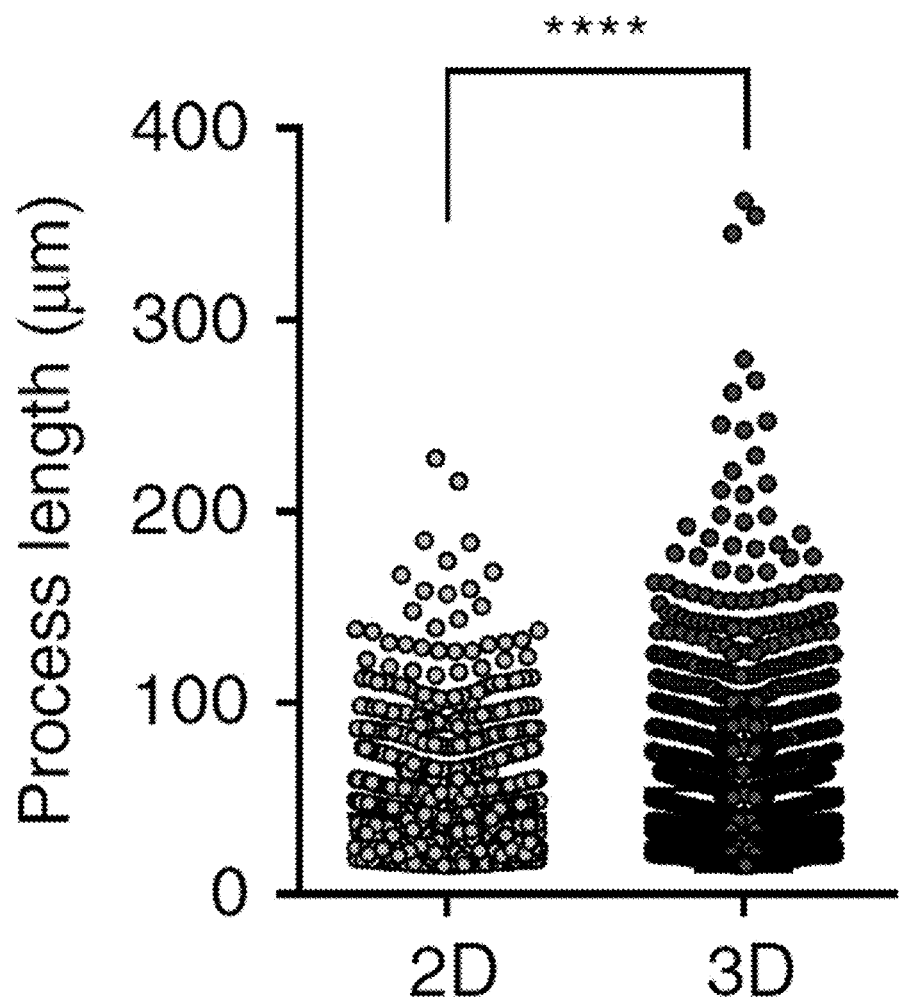
FIG. 38 is a graph comparing the process length of human astrocytes (HA) cultured on the 2D Matrigel-coated surface and inside the 3D Matrigel.

As shown in FIGS. 36 to 38, when human astrocytes (HA) were cultured on the 2D Matrigel-coated surface, a flat polygonal enlarged cell body shape having short processes was shown. On the other hand, when human astrocytes (HA) were cultured inside the 3D Matrigel, a small cell body shape having thin and long processes distributed radially was observed.

Comparison of Function of Astrocytes According to Culture Method

The gene expression level of the reactive gliosis marker in 2D or 3D cultured human astrocytes (HA) was confirmed through qRT-PCR analysis. To analyze glial reactivity of HA in 2D and 3D culture system (n=4), standard qRT-PCR was performed with a StepOnePlus Real-Time PCR system (Applied Biosystems) using TaqMan Fast Universal PCR Master Mix (Applied Biosystems). The target genes were assessed using commercially available primers, and the primers used in the experiment are shown in Table 2 below.

TABLE 2

| Experiment | Gene Symbol | Gene Name | TaqMan Assay ID # |
|---|---|---|---|
| Control HA RT-qPCR | GAPDH | Glyceraldehyde-3-phosphate dehydrogenase | Hs02786624_g1 |
| | GFAP | Glial fibrillary acidic protein | Hs00909233_m1 |
| | VIM | Vimentin | Hs00958111_m1 |
| | LCN2 | Lipocalin-2 | Hs01008571_m1 |

Figure 39:
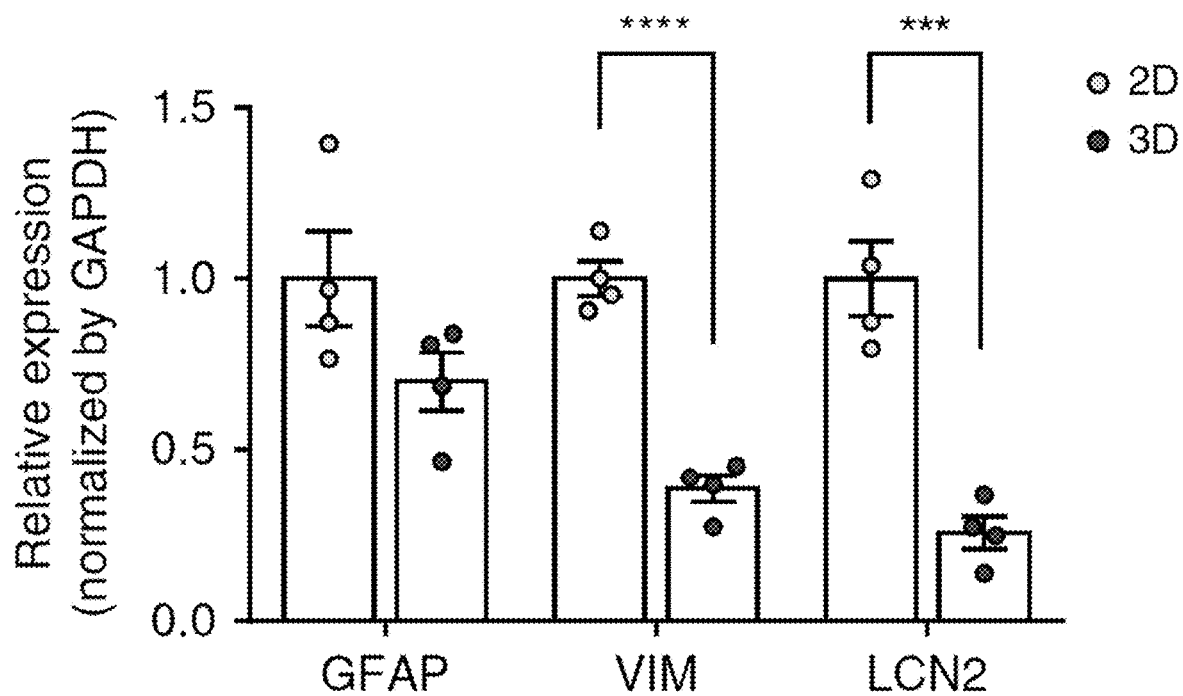
FIG. 39 is a graph comparing the expression level of GFAP, VIM, and LCN2 in human astrocytes (HA) cultured on the 2D Matrigel-coated surface and inside the 3D Matrigel (n=4, *p<0.005, **p<0.001 by student t-test).

As shown in FIG. 39, it was confirmed that the expression of vimentin (VIM) and lipocalin-2 (LCN2), which are reactive gliosis markers, was significantly reduced in 3D cultured human astrocytes (HA) compared to 2D cultured human astrocytes (HA). LCN2 is a gene that plays an important role in neuroinflammation by mediating the pro-inflammatory response, and is known to increase its expression in reactive astrocytes. On the other hand, there was no significant difference in the expression level of glial fibrillary acidic protein (GFAP), which is a representative astrocyte marker.

Figure 40:
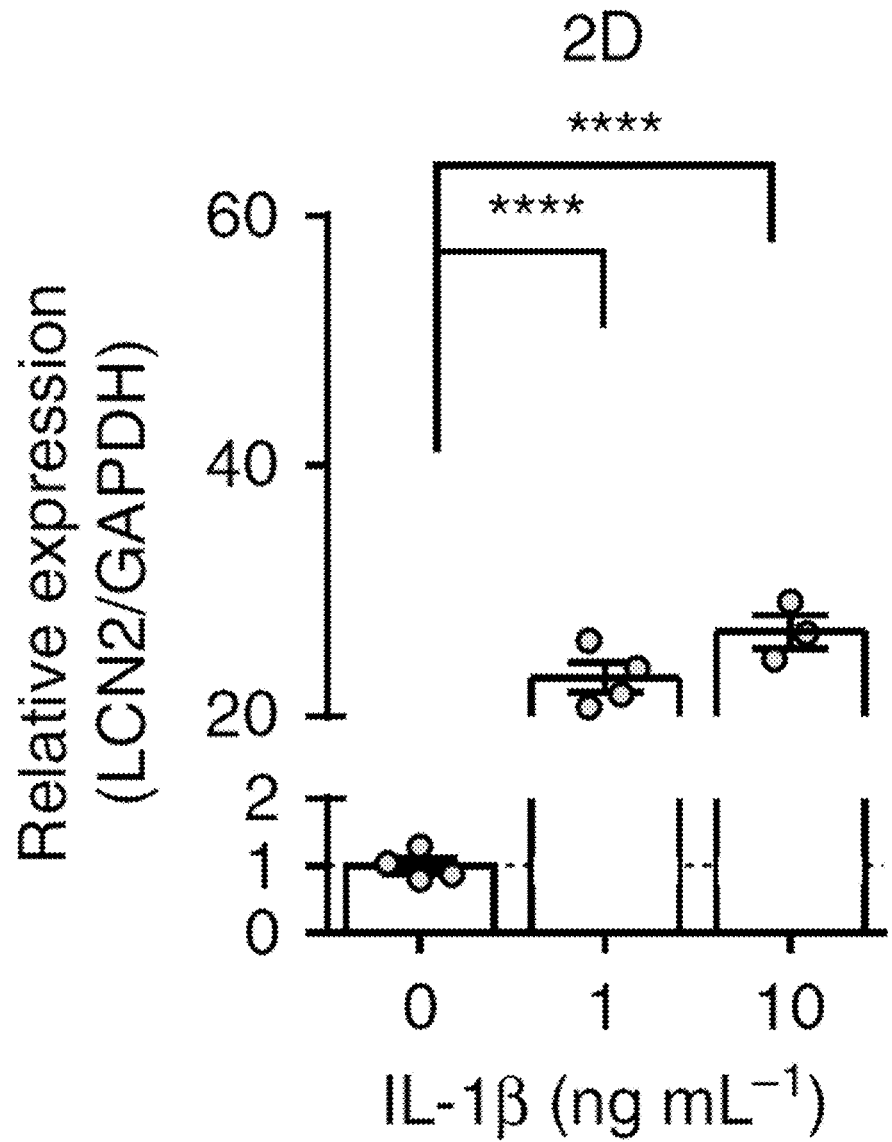
FIG. 40 is a graph comparing the expression level of LCN2 according to the concentration of IL-1β treated on human astrocytes (HA) cultured on the 2D Matrigel-coated surface.
Figure 41:
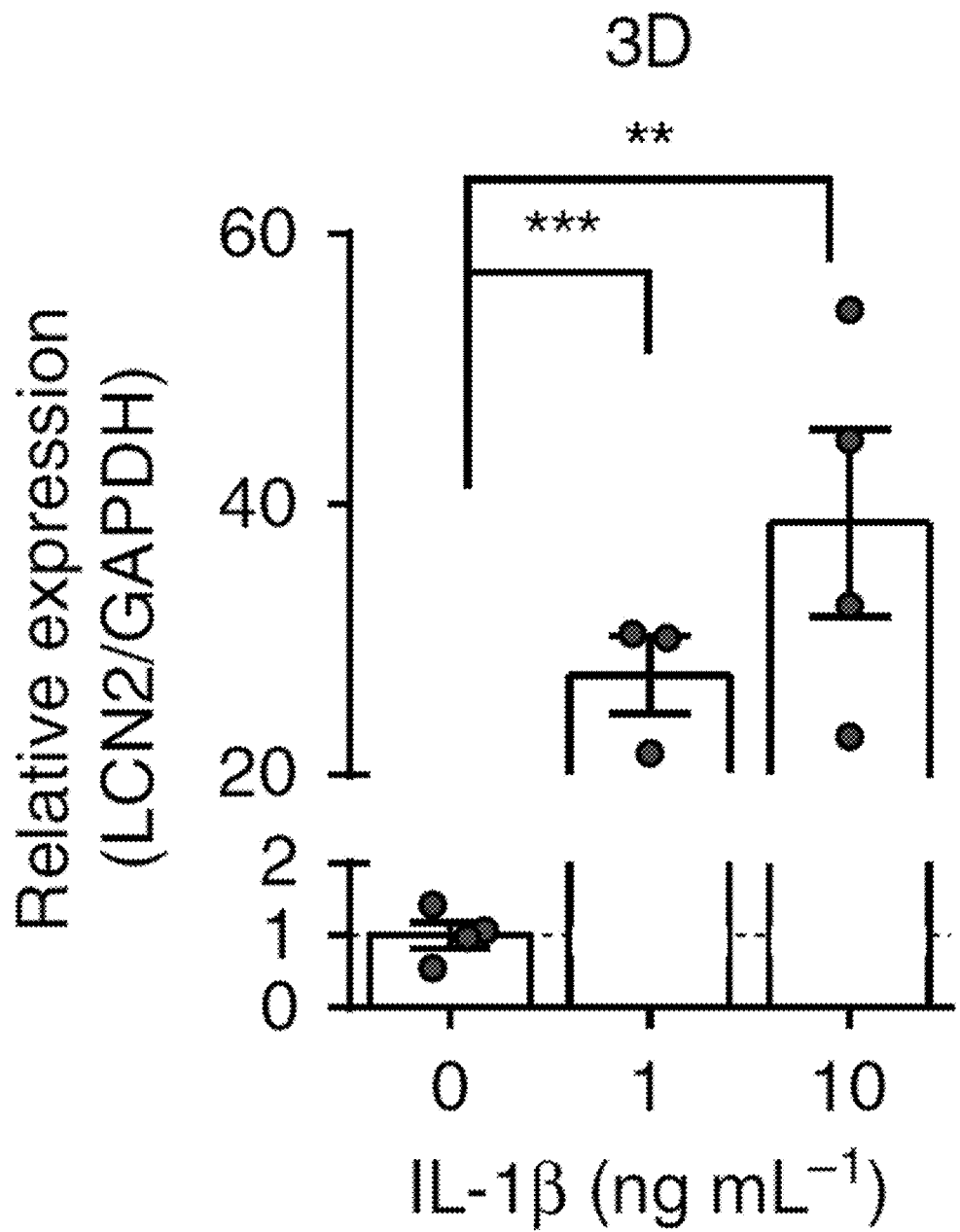
FIG. 41 is a graph comparing the expression level of LCN2 according to the concentration of IL-1β treated on human astrocytes (HA) cultured inside the 3D Matrigel.

In addition, as shown in FIGS. 40 and 41, it was confirmed that the expression level of LCN2 was dose-dependently controlled in both 2D and 3D cultures when treated with interleukin-1β (IL-1β), which is an inflammatory cytokine.

Therefore, it was confirmed that the 3D cultured human astrocytes (HA) exhibited similar morphology and gene expression to astrocytes in vivo compared to 2D culture, and thus were suitable for simulating the structure and function of the blood-brain barrier.

Example 8: Comparison of Expression of AQP-4 and α-Syn According to Astrocyte Culture Method In the astrocyte culture in the second central channel of the microfluidic device simulating blood-brain barrier (BBB) prepared in Example 2 comprising human brain microvascular endothelial cells (HBMEC), human brain vascular pericytes (HBVP) and human astrocytes (HA), the expression of Aquaporin-4 (AQP-4) and α-syn (α-syntrophin) according to 2D culture and 3D culture was compared. Astrocytes in the perivascular space control water homeostasis in the brain through AQP-4, which is a water channel protein of the terminal processes, and thus the polarization of AQP-4 in the astrocytic end-feet processes plays an important role in simulating the homeostasis control and physiological conditions of the blood-brain barrier. α-syn is known as an anchor that controls the polarization of AQP-4 to the astrocytic end-feet.

To visualize cell-specific marker expression, human astrocyte (HA) samples in 2D and 3D cultures cultured in Example 7 were fixed with 2% paraformaldehyde (PFA; Santa Cruz Biotechnology, San Diego, CA, USA) for 15 min at room temperature. After permeabilizing in 0.1% Triton X (Sigma-Aldrich) in PBS for 15 min, the samples were blocked with 2% bovine serum albumin (BSA; Sigma-Aldrich) in PBS for 1 h at room temperature. Subsequently, the samples were incubated with primary antibodies at 4° C. overnight, washed three times with 1% BSA. They were treated with GFAP, AQP4, and α-syn antibodies, respectively, at 4° C. for 6 h. Nuclei were counterstained with 4,6-diamino-2-phenylindole (DAPI; Invitrogen) and stored in PBS before imaging. Fluorescently visualized samples were examined using a confocal microscope (LSM 700, Carl Zeiss, Oberkochen, Germany).

Figure 42:
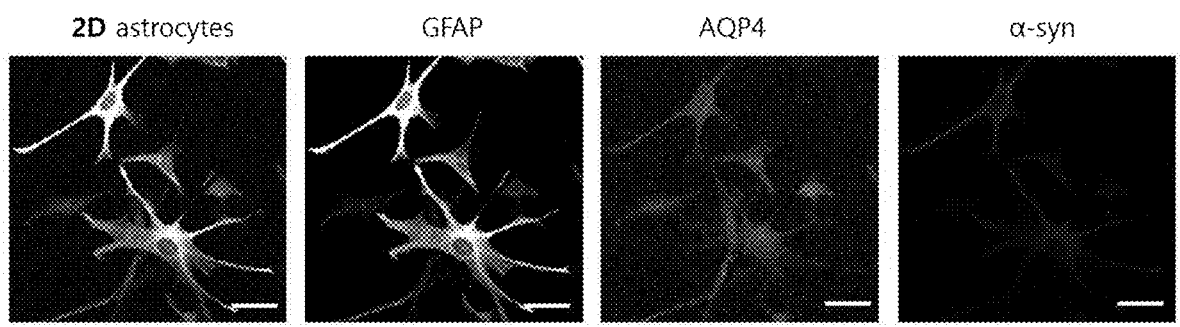
FIG. 42 shows the expression of AQP-4 and α-syn when astrocytes are cultured on the 2D Matrigel-coated surface (Scale bars=50 μm).
Figure 43:
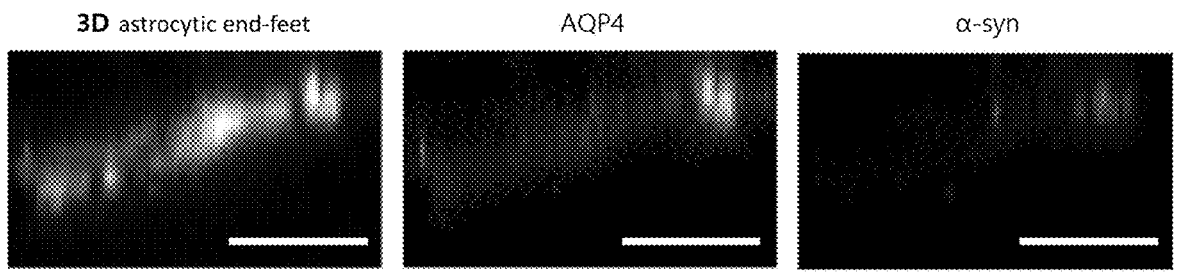
FIG. 43 shows the expression of AQP-4 and α-syn when astrocytes are cultured inside the 3D Matrigel (Scale bars=20 μm).

As shown in FIGS. 42 and 43, it was confirmed that when astrocytes were cultured in 2D, AQP-4 and α-syn were expressed in a diffused form, whereas when cultured in 3D, they were polarized to the astrocytic end-feet.

Therefore, it was confirmed that the 3D cultured human astrocytes (HA) performed a function similar to that of the astrocytes in vivo compared to 2D culture, and thus was a suitable form in simulating the function of the blood-brain barrier.

Example 9: Comparison of AQP-4 Expression According to Cultured Cells

The AQP-4 expression polarization level was confirmed in the microfluidic device simulating blood-brain barrier (BBB) prepared in Example 2 comprising human brain microvascular endothelial cells (HBMEC), human brain vascular pericytes (HBVP) and human astrocytes (HA). For comparison, the AQP-4 expression was confirmed together when only human astrocytes (HA) were cultured, and when human astrocytes (HA) and human brain microvascular endothelial cells (HBMEC) were cultured.

After visualizing the AQP-4 expression in each sample in the same manner as in Example 8, distribution of AQP4 was quantified by measuring the fluorescence intensity profile along the z-axis in z-stack images of the perivascular channel using ImageJ (NIH, Bethesda, MD, USA). After calculating the average of the fluorescence intensity in each of the channel included in the insert (vascular) and the channel included in the base (parenchymal), the average of the fluorescence intensity in the channel included in the insert (vascular) was divided by the average of the fluorescence intensity in the channel included in the base (parenchymal) to calculate the AQP-4 polarization index.

Figure 44:
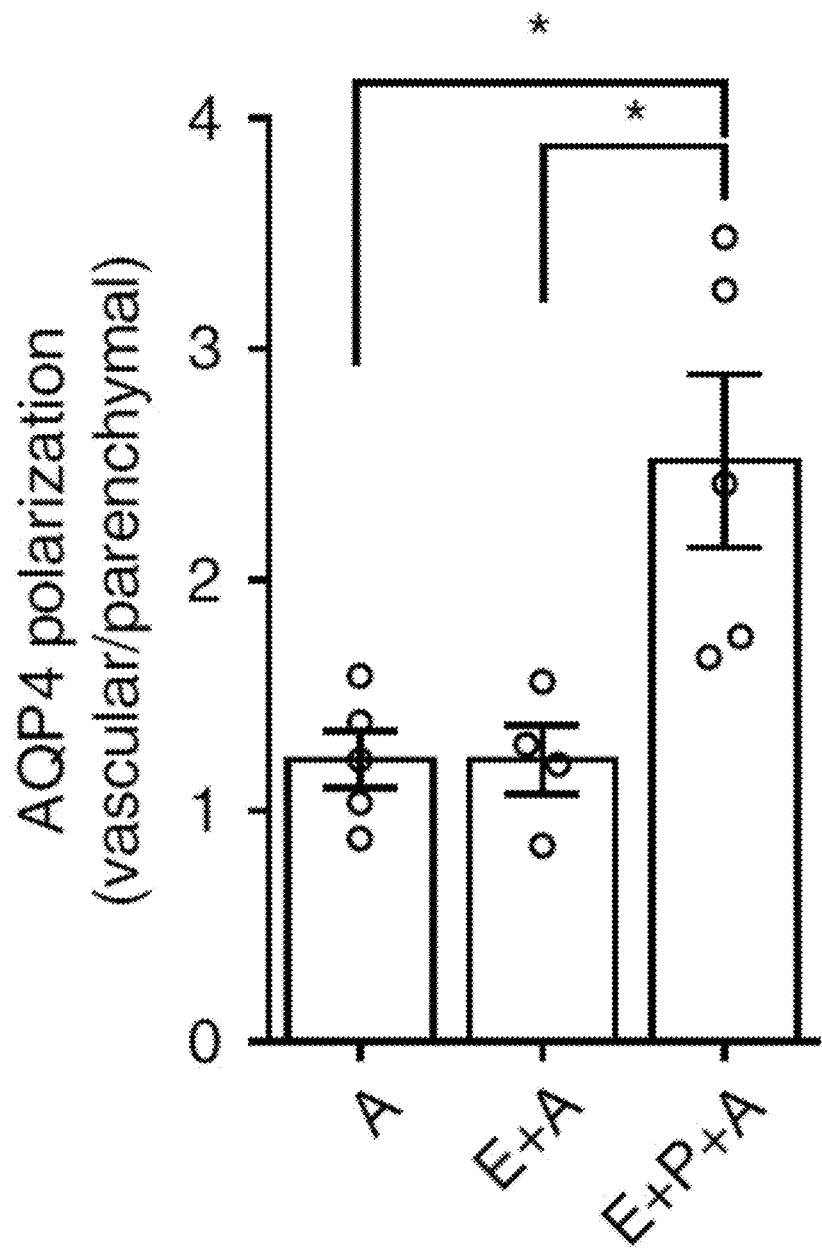
FIG. 44 is a graph showing the polarization level of AQP-4 when only human astrocytes (HA) are cultured (A), when human astrocytes (HA) and human brain microvascular endothelial cells (HBMEC) are cultured (E+A), and when human brain microvascular endothelial cells (HBMEC), human brain vascular pericytes (HBVP) and human astrocytes (HA) are cultured together (E+P+A) (n=4, *p<0.05 by student t-test).

As shown in FIG. 44, it was confirmed that the polarization level of AQP-4 was increased when human brain microvascular endothelial cells (HBMEC), human brain vascular pericytes (HBVP) and human astrocytes (HA) were cultured together (E+P+A) compared to when only human astrocytes (HA) were cultured (A) or when human astrocytes (HA) and human brain microvascular endothelial cells (HBMEC) were cultured (E+A).

Therefore, it was confirmed that the polarization of AQP-4 was significantly induced in the presence of pericytes, and it was confirmed that the water transport system of the blood-brain barrier (BBB) could be simulated when human brain microvascular endothelial cells (HBMEC), human brain vascular pericytes (HBVP) and human astrocytes (HA) are cultured together.

Example 10: Analysis of Nanoparticle Transport Through Blood-Brain Barrier (BBB)

The transport of nanoparticles through a structure simulating blood-brain barrier was monitored and quantified in the microfluidic device simulating blood-brain barrier (BBB) prepared in Example 2 comprising human brain microvascular endothelial cells (HBMEC), human brain vascular pericytes (HBVP) and human astrocytes (HA). In the study of drug delivery in the central nervous system, quantifying the transport of drug-containing compounds to the brain at the cellular and molecular level is an important task.

Synthesis of HDL Mimicking Nanoparticle eHNP-A1

Figure 45:
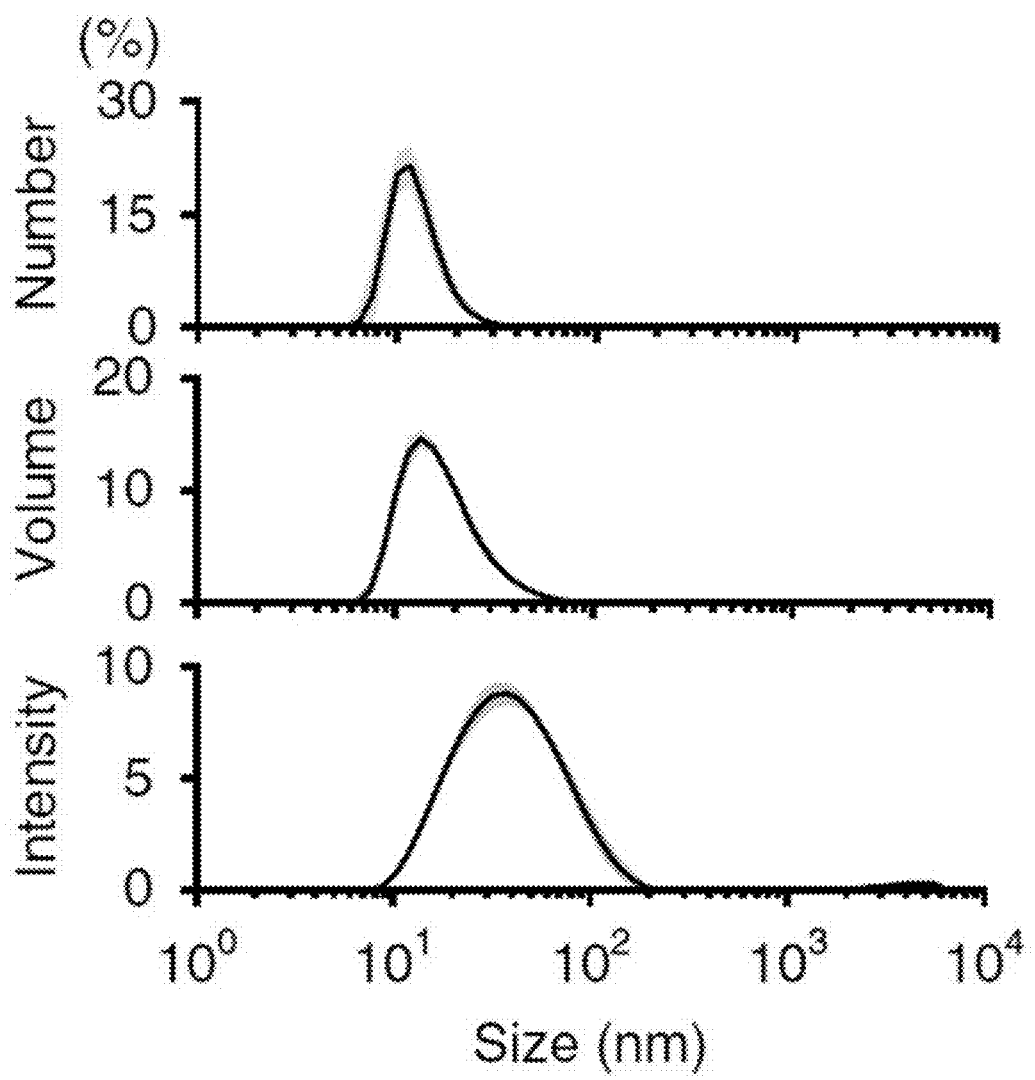
FIG. 45 is a graph showing the size distribution of synthesized eHNP-A1.

HDL mimicking disc-shaped nanoparticle eHNP-A1 composed of lipid (DMPC), apolipoprotein A1, and a fluorescence marker was synthesized in a physiologically appropriate size and configuration using microfluidic technology. The size distribution of the synthesized eHNP-A1 was measured and shown in FIG. 45.

Confirmation of Biodistribution of Systemically Administered eHNP-A1

1 mg/kg of eHNP-A1 was systemically administered to the mouse via tail vein injection. Injection of 200 μL saline was served as control. 24 h after administration, mice were sacrificed and perfused with saline and 4% PFA for 15 min. Then organs (brain, heart, lung, liver, kidneys, and spleen) were harvested to visualize their DiR content using an in vivo imaging system (IVIS; Perkin Elmer, Waltham, MA, USA). To visualize the eHNP-A1 internalization inside the brain tissue, the harvested brain tissues were cryosectioned into 10 μm slices and stained with DAPI using the DAPI-containing antifade mounting medium (H-1200; Vector Laboratories, Burlingame, CA, USA). The slides were then imaged under a confocal microscope (Zeiss LSM 780).

Figure 46:
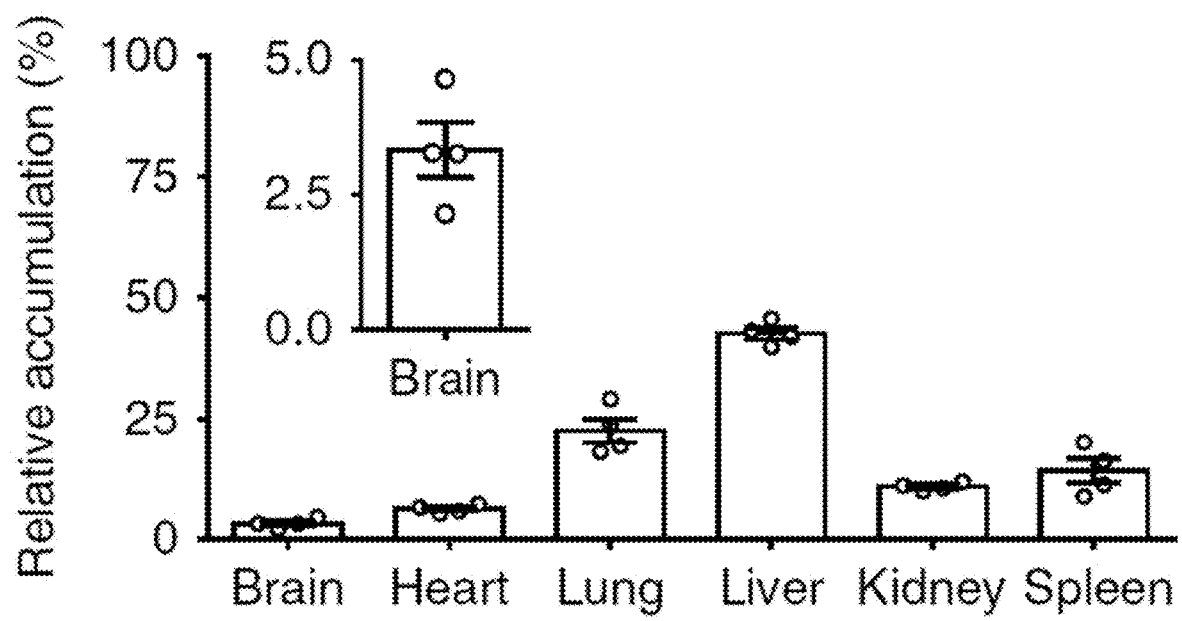
FIG. 46 is a graph showing the quantification of the relative distribution of eHNP-A1 in each organ in vivo (mean±s.e.m, n=4).
Figure 47:
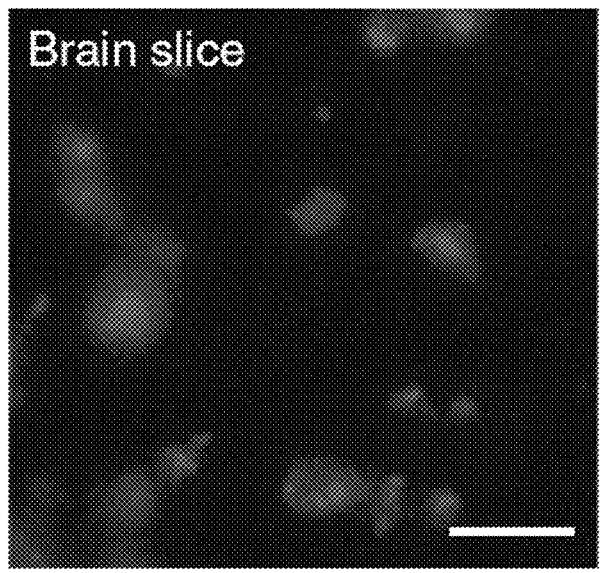
FIG. 47 shows the distribution of eHNP-A1 in the brain.

As a result, as shown in FIG. 46, it was confirmed that the amount of eHNP-A1 accumulated in the brain was at most 3% of the systemic accumulation amount. In addition, as shown in FIG. 47, it was confirmed that the systemically administered eHNP-A1 was locally distributed around the cell nucleus of the brain.

Distribution of eHNP-A1 in Microfluidic Device Simulating Blood-Brain Barrier

In order to quantify the distribution of eHNP-A1 in the microfluidic device simulating blood-brain barrier (BBB) prepared in Example 2 and confirm material transport mechanism, eHNP-A1 in the first central channel (vascular) was incubated for 2 h. In addition, in order to test whether eHNP-A1 passes through the blood-brain barrier through transcytosis, one of the major transport mechanism of HDL, using scavenger receptor class B type 1 (SR-B1), an HDL receptor of brain endothelial cells, SR-B1 was blocked by treatment with BLT-1 (block lipid transporter-1). Thereafter, the relative fluorescence intensity of the culture medium comprising eHNP-A1 sampled from each of the first central channel (vascular) and the second central channel (perivascular) was measured. In addition, a FACS (fluorescence-activated cell sorting) analysis was performed on the distribution of human brain microvascular endothelial cells (HBMEC), human astrocytes (HA), and human brain vascular pericytes (HBVP), which are eHNP-A1 positive.

Figure 48:
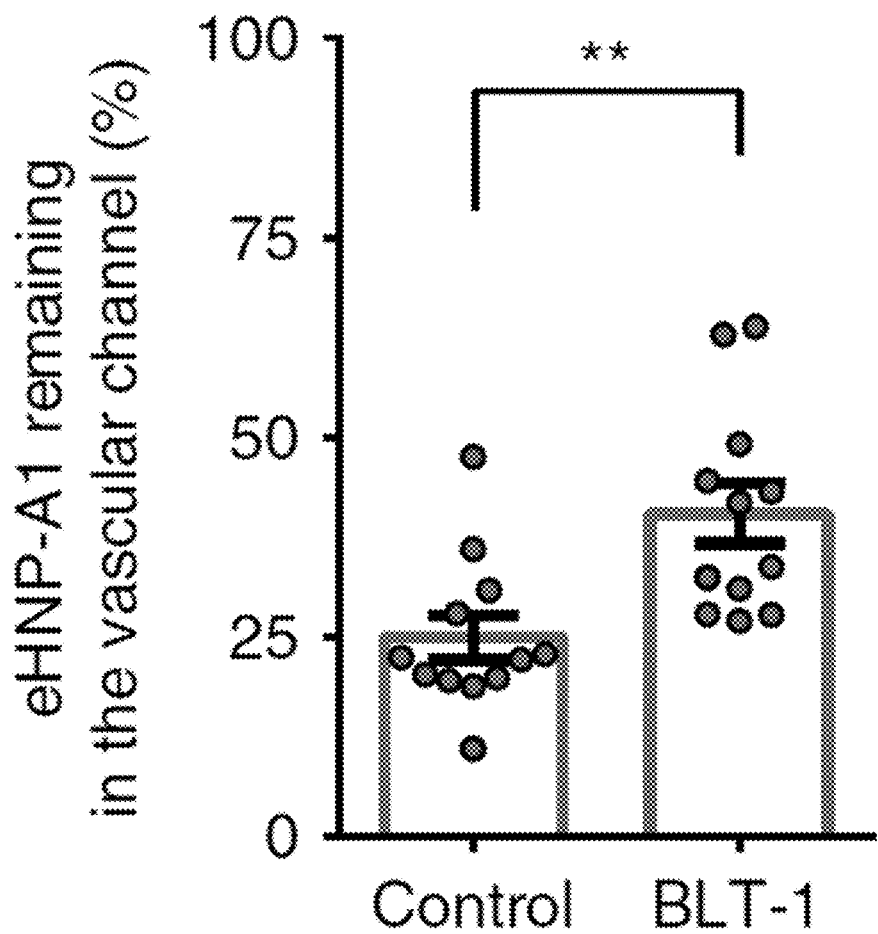
FIG. 48 is a graph showing the relative fluorescence intensity of the culture medium comprising eHNP-A1 sampled from a first central channel (vascular channel) (n=12; **p<0.01 by student t-test, mean±s.e.m.).
Figure 49:
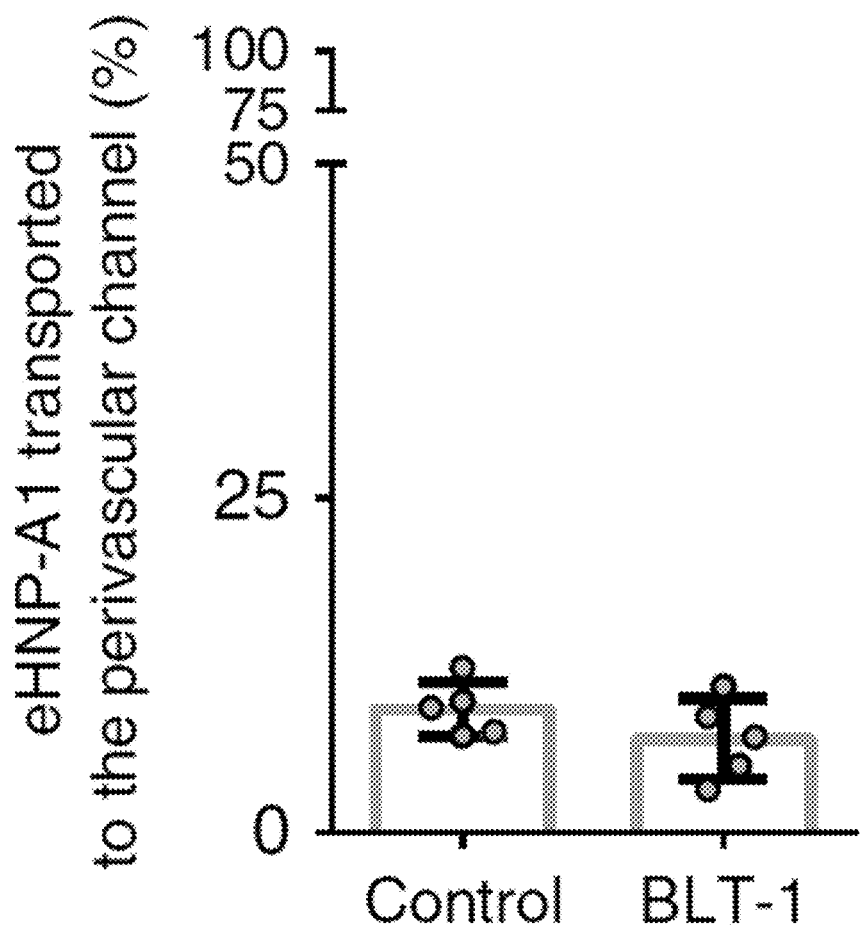
FIG. 49 is a graph showing the relative fluorescence intensity of the culture medium comprising eHNP-A1 sampled from a central channel (perivascular channel) (n=5).
Figure 50:
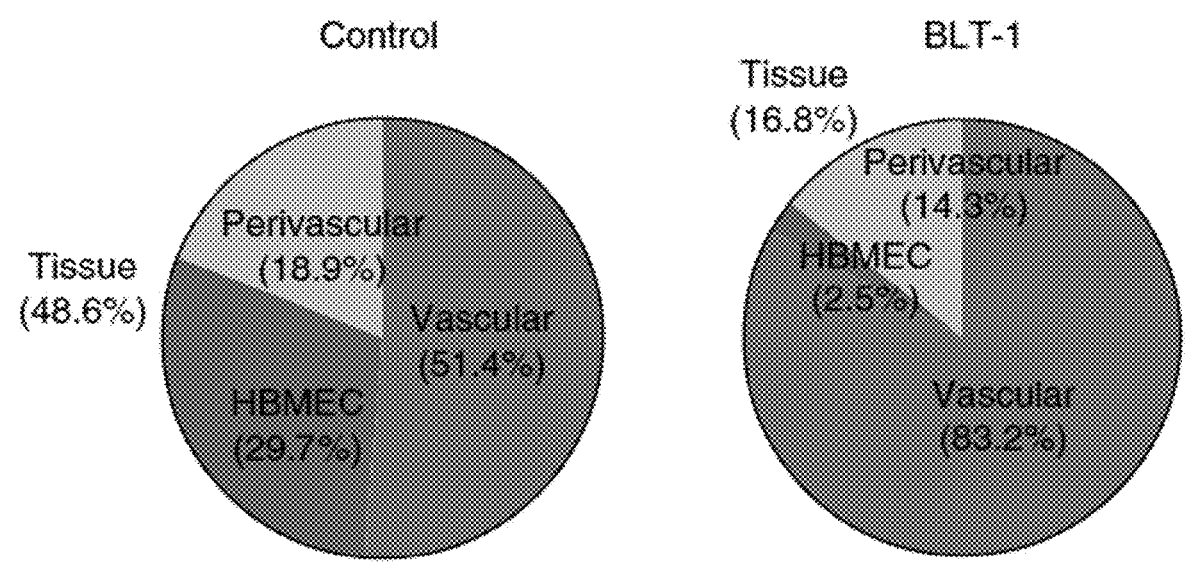
FIG. 50 is a graph showing the distribution of eHNP-A1 in a first central channel (vascular), human brain microvascular endothelial cells (HBMEC), and a second central channel (perivascular).
Figure 51:
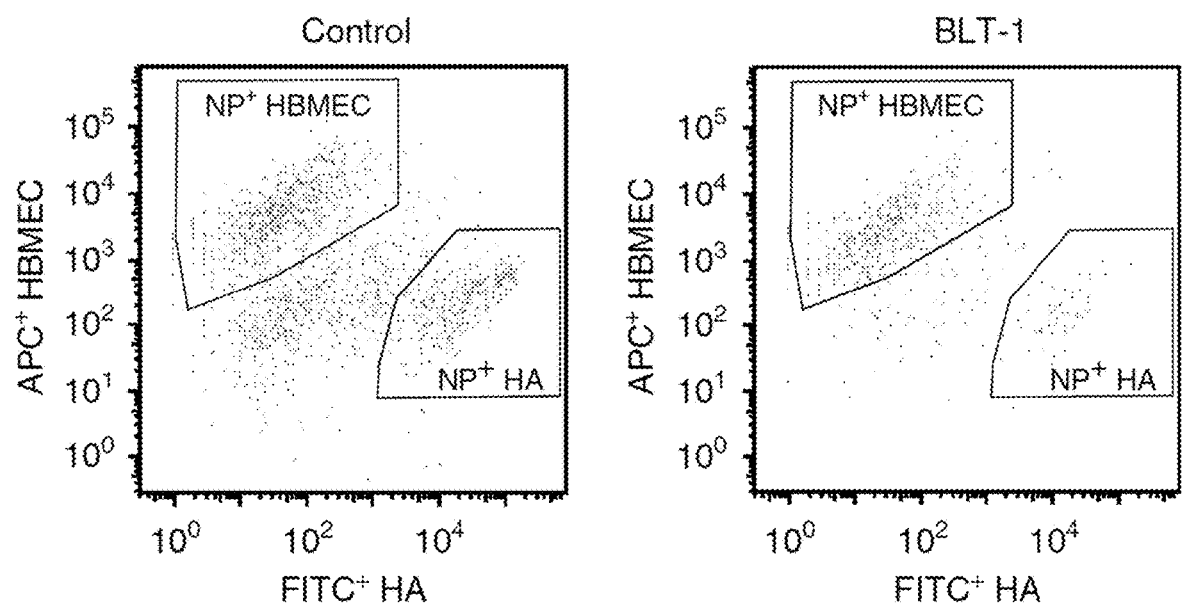
FIG. 51 is a FACS (fluorescence-activated cell sorting) plot for the number of human brain microvascular endothelial cells (HBMEC), human astrocytes (HA), and human brain vascular pericytes (HBVP), which are eHNP-A1 positive.
Figure 52:
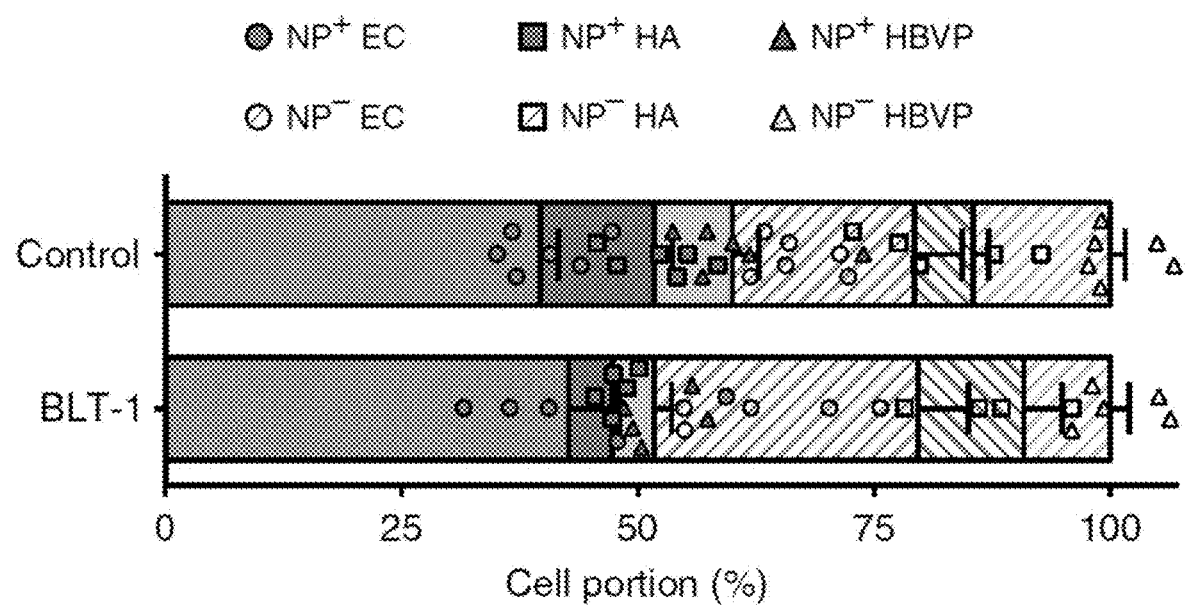
FIG. 52 is a graph quantifying the cell portions observed in FIG. 51.

As shown in FIGS. 48 and 49, after SR-B1 was blocked, the amount of eHNP-A1 remaining in the first central channel was significantly increased, whereas the amount of eHNP-A1 transported to the second central channel did not change significantly. In addition, as shown in FIG. 50, it was confirmed that the amount of eHNP-A1 absorbed by human brain microvascular endothelial cells (HBMEC) or transported to the second central channel upon treatment with BLT-1 was reduced by about 3 times, and as shown in FIGS. 51 and 52, it was confirmed that the total eHNP-A1 positive cells were reduced upon treatment with BLT-1.

Therefore, it was confirmed that the interaction between cells and nanoparticles can be monitored and the distribution of nanoparticles can be quantified using the microfluidic device simulating blood-brain barrier (BBB) prepared in Example 2.

The invention claimed is:

1. A microfluidic device comprising:
an insert comprising a first central channel;
a base comprising a second central channel, a third side channel, a fourth side channel, a fifth passage channel connecting the second central channel and the third side channel, and a sixth passage channel connecting the second central channel and the fourth side channel; and
a porous membrane positioned between the insert and the base,
wherein the third side channel and the fourth side channel have a lower channel height than the second central channel, wherein the base further comprises a first fluid reservoir and a second fluid reservoir, and wherein the base comprises a seventh passage channel connecting the third side channel and the first fluid reservoir, and an eighth passage channel connecting the fourth side channel and the second fluid reservoir.

2. The microfluidic device according to claim 1, wherein the insert is detachable from the base.

3. The microfluidic device according to claim 2, wherein the base comprises a groove into which the insert is capable of being inserted.

4. The microfluidic device according to claim 2, wherein the insert comprises a first fastening head,
the base comprises a second fastening head, and
the first fastening head and the second fastening head are hooked to each other so that the insert and the base are attached and detached by a snap fit.

5. The microfluidic device according to claim 1, wherein the third side channel and the fourth side channel do not contact the porous membrane.

6. The microfluidic device according to claim 1, wherein the first central channel, the second central channel, the third side channel, and the fourth side channel comprise an inlet and an outlet capable of inducing and controlling the perfusion of a liquid agent.

7. The microfluidic device according to claim 1, wherein the fifth passage channel and the sixth passage channel have a lower channel height than the second central channel, the third side channel, and the fourth side channel.

8. The microfluidic device according to claim 1, wherein the seventh passage channel and the eighth passage channel have a lower channel height than the second central channel, the third side channel, and the fourth side channel.

9. The microfluidic device according to claim 1, wherein the seventh passage channel and the eighth passage channel are formed perpendicular to a direction of the second central channel.

10. The microfluidic device according to claim 1, wherein the microfluidic device is made of plastic, glass, metal, or silicon.

11. The microfluidic device according to claim 1, wherein the first central channel comprises tissue barrier cells.

12. The microfluidic device according to claim 11, wherein the tissue barrier cells are one or more selected from vascular endothelial cells; skin cells; cancer cells; secretory gland cells; muscle cells; and epithelial cells of bronchi, large intestine, small intestine, pancreas, and kidney.

13. The microfluidic device according to claim 1, wherein the second central channel comprises internal tissue cells and hydrogel.

14. The microfluidic device according to claim 13, wherein the internal tissue cells are one or more selected from astrocytes, pericytes, nerve cells, neural stem cells, glial cells, cardiac myocytes, smooth muscle cells, intestinal epithelial cells, keratinocytes, skin fibroblasts, podocytes, and glomerular endothelial cells.

15. The microfluidic device according to claim 13, wherein the hydrogel is one or more selected from collagen, laminin, hyaluronic acid, mineral, fibrin, fibronectin, elastin, peptide, polyethylene glycol, and alginate.

16. The microfluidic device according to claim 1, wherein one or more cells selected from cells included in the first central channel, cells included in the second central channel, and cells attached to the porous membrane are capable of being separated by separating the insert from the base.

* * * * *